United States Patent [19]
Turner et al.

[11] Patent Number: 5,591,606
[45] Date of Patent: * Jan. 7, 1997

[54] PROCESS FOR THE PRODUCTION OF A83543 COMPOUNDS WITH *SACCHAROPOLYSPORA SPINOSA*

[75] Inventors: Jan R. Turner, Carmel; Mary L. B. Huber, Danville; Mary C. Broughton; Jon S. Mynderse, both of Indianapolis; James W. Martin, Coatesville, all of Ind.

[73] Assignee: DowElanco, Indianapolis, Ind.

[ * ] Notice: The term of this patent shall not extend beyond the expiration date of Pat. No. 5,202,242.

[21] Appl. No.: 397,306

[22] Filed: Mar. 2, 1995

Related U.S. Application Data

[63] Continuation of Ser. No. 973,121, Jun. 11, 1992, abandoned.

[51] Int. Cl.$^6$ .............. C12P 19/62; C12P 19/60
[52] U.S. Cl. .............. 435/76; 435/75; 435/822
[58] Field of Search .................. 435/76, 75, 822

[56] References Cited

U.S. PATENT DOCUMENTS

| | | | |
|---|---|---|---|
| 2,881,162 | 4/1959 | Walasek | 260/210 |
| 3,725,385 | 4/1973 | Freiberg | 260/210 AB |
| 4,148,883 | 4/1979 | Celmer et al. | |
| 4,206,206 | 6/1980 | Mori et al. | |
| 4,213,966 | 7/1980 | Liu et al. | 424/123 |
| 4,224,314 | 9/1980 | Celmer et al. | |
| 4,251,506 | 2/1981 | Laby | 424/19 |
| 4,251,511 | 2/1981 | Whaley et al. | |
| 4,273,920 | 6/1981 | Nevin | 528/361 |
| 4,293,651 | 10/1981 | Whaley et al. | |
| 4,321,329 | 3/1982 | Whaley et al. | |
| 4,366,308 | 12/1982 | Soma et al. | 536/128 |
| 4,421,760 | 12/1983 | Box | 424/274 |
| 4,448,970 | 5/1984 | Magerlein | |
| 4,482,707 | 11/1984 | Sakakibara et al. | 536/16.8 |
| 4,501,752 | 2/1985 | Yokoi et al. | |
| 4,508,647 | 4/1985 | Hatori et al. | 260/239.3 T |
| 4,514,562 | 4/1985 | Toscaro | 336/7.4 |
| 4,515,942 | 5/1985 | Iwasaki et al. | |
| 4,530,835 | 7/1985 | Bunge et al. | 424/117 |
| 4,560,509 | 12/1985 | Johnson et al. | 260/239.3 P |
| 4,568,740 | 2/1986 | Oppici et al. | 536/7.5 |
| 4,764,602 | 8/1988 | Kumagai et al. | 536/7.1 |
| 4,831,016 | 5/1989 | Mrozik et al. | 514/30 |
| 5,003,056 | 3/1991 | Nishikiori et al. | 536/71 |
| 5,028,536 | 7/1991 | Golik et al. | 435/101 |
| 5,202,242 | 4/1993 | Mynderse | 435/76 |
| 5,227,295 | 7/1993 | Baker | 435/76 |
| 5,362,634 | 11/1994 | Boeck et al. | 435/76 |

FOREIGN PATENT DOCUMENTS

| | | |
|---|---|---|
| 0214731A3 | 3/1987 | European Pat. Off. |
| 375316 | 12/1989 | European Pat. Off. |
| 55-000310 | 1/1980 | Japan |
| 59-151896 | 8/1984 | Japan |
| 59-170092 | 9/1984 | Japan |
| 60-053597 | 11/1985 | Japan |
| 2059767 | 9/1979 | United Kingdom |
| 9106552 | 5/1991 | WIPO |
| WO93/09126 | 5/1993 | WIPO |

OTHER PUBLICATIONS

Kirst et al., Tetrahedon Letters (1991), 32(37):4839–4842.
Whaley et al., Tetrahedron Letters (1980), 21:3659.
Kreuzman et al., J. Biological Chemistry (1988), 263(30):15626–15633.
Snyder et al., J. Am. Chem. Soc., (1984), 106:787.
Mertz and Yao, Int'l J of Systematic Bacteriology (1990), 40(1):34–39.
Celmer et al., J. Chem. Soc. (1980) 102:4203.
Aizawa et al. (1979), The Journal of Antibiotics, 22(3):193–196.
Ikeda, et al. (1985), J. Antibiotic, 38:436.
Jomon et al., (1972), The Journal of Antibiotics, 25(5):271–280.
Dybas and Babu (1988), Brighton Crop Protection Conference, 57–64.
Borchardt et al. (1979), Biochem. & Biophys. Res. Comm., 89(3):919–924.
Vedel et al., (1978), Biochem. & Biophys. Res. Comm., 85(1):371–376.
Pickett, J. A., (1988), Chemistry in Britain, 137–142.
Omura, (1984), Macrolide Antibiotics, Chapter 13.
Fuller (1978), Biochemical Pharmacology, 27:1981–1983.
Jackson et al. (1988), Abstracts of the 1988 ICAAC, 26026.
Umezawa (1980), The Journal of Antibiotics, 33(3):15–26.
Umezawa, Index of Antibiotics from Actinomycetes, vol. 2.
Omura and Tannaka (1984), Macrolide Antibiotics, Chapter 1.
Schulman and Ruby (1987), Antimicrobial Agents and Chemotherapy, 31(6):964–965.
Schulman et al. (1985), The Journal of Antibiotics, 1494–1498.
Ito and Hirata (1972), Tetrahedron Letters, 12:1185–1188.
Aizawa et al. (1979), J. Antibiot., 32:193.
Ito et al. (1972), Tetrahedron Letters, 1181, 1185, 2557.
Derwent Abstract 84–278337/45, SSSE Mar. 16, 1983.
Derwent Abstract 84–252941/41, SSSE Feb. 16, 1983.
Derwent Abstract 92:144960k.
Derwent Abstract 11667c/07, KAKE May 31, 1978.
Derwent Abstract 92:211459u.
Derwent Abstract 88–095030/14, SSSE 00.00.86.
Derwent Abstract 85–245719/40, SSSE 01.02.84.

(List continued on next page.)

*Primary Examiner*—Irene Marx
*Attorney, Agent, or Firm*—Andrea T. Borucki

[57] ABSTRACT

New A83543 components, including fermentation products A83543Q, A83543R, A83543S and A83543T and N-demethyl derivatives, and salts thereof, are useful for the control of insects and mites. The pseudoaglycones are useful for the preparation of A83543 components. Methods for making the new A83543 components by culture of *Saccharopolyspora spinosa* NRRL 18823 are provided. Insecticidal and ectoparasiticidal compositions containing new A83543 components are also provided.

5 Claims, 9 Drawing Sheets

OTHER PUBLICATIONS

Derwent Abstract 54333S–BCD, Fuji, 17.02.69.

Derwent Abstract 80–11667C/07.

Catalogue of Bacteria and phages, ATCC, 7th Ed., 1989, p. 190.

Umezawa, Institute of Microbial Chemistry, Tokyo, Index of Antibi. from Actinomycetes, vol. 1 pp. 57–64.

Sakano et al. (1980), J. Antibiot. (Tokyo), 33(7):683–689.

Brown, et al. (1986), J. Liq. Chromatography, 9(4):831–844.

Chen et al. (1981), Acta Microbiol. Sin., 21(2):192–196 (Biosis abstract).

Drioli (1986), Separation, Recovery and Purification in Biotechnology, 52–66.

Kubo et al. (1985), Analytical Letters, 18(B3):245–260.

Brode et al. (1986), Arzneim–Forsch, 36(3):437–442.

Julien et al. (1988), Clin. Chem., 34(5):966–969.

Chemical Abstracts, vol. 87, No. 24, Dec. 1977, R. Datta et al., "Concentration of Antibiotics by Reverse Osmosis." See p. 310, see the Abstract No. 189423a, Biotechnol. Bioeng. 1977, vol. 19, No. 10, 1419–1429.

Cram et al. (1964), Organic Chemistry, 2nd ed., p. 204.

Journal of American Chemical Society (1992), vol. 114, No. 6, pp. 2260–2262, Evans et al., "Asymmetric Synthesis of the Macrolide (+)–A83543A (Lepicidin) Aglycone." See the whole document.

Chemical Abstracts (1991), vol. 114, No. 80066m, Boeck et al.

ACS Symposium Series, Synthesis and Chemistry of Agrochemicals III, vol. 504, 1992, pp. 214–225, Kirst et al., "Discovery, Isolation, and Structure Elucidation of a Family of Structurally Unique, Fermentation–Derived Tetracyclic Macrolides." See abstract. See p. 216, paragraph 2; p. 217, paragraph 1.

Jacobson, G. K., "Mutations," Chapter 5b of *Biotechnology*, vol. 1, H.–J. Rehm and G. Reeds, eds. (1981).

Journal of the Chemical Society (1964), London, GB, Birch et al., "Studies in Relation to Biosynthesis." Part XXXV. Macrolide Antibiotics to Biosynthesis. Part XII. Methymycin, pp. 5274–5278.

Chemical Abstracts (1979), vol. 90, No. 19, p. 591, Column 2–p. 592, col. 1, Abstract No. 151957b, Columbus, OH; Inanaga et al., "Synthesis of Methynolide," & Tennen Yuki Kagobutsu Toronkai Koen Yoshishu, 21st 1978, 324–30 (abstract).

Pickett, J. A. (1988), Chemistry in Britain, 137–142.

PROCESS FOR THE PRODUCTION OF A83543 COMPOUNDS WITH *SACCHAROPOLYSPORA SPINOSA*

CROSS-REFERENCE TO RELATED APPLICATION

This is a continuation of application Ser. No. 07/973,121 filed Jun. 11, 1992, which is now abandoned.

FIELD OF THE INVENTION

The invention relates to new components of fermentation product A83543.

BACKGROUND OF THE INVENTION

Target insects are rapidly developing resistance to the insecticides which are presently available. Resistance to insecticides in arthropods is widespread, with at least 400 species exhibiting resistance to one or more insecticides. The development of resistance to older insecticides, such as DDT, the carbamates, and the organophosphates, is well documented (see Brattsten, et al. (1986), *Science*, 231:1255). Resistance to synthetic insecticides has developed extremely rapidly, including the development of resistance to the newer pyrethroid insecticides (see Pickett (1988), *Chem. Britain*, 137). Therefore, new insecticides are in demand.

Fermentation product A83543, a family of related compounds produced by *Saccharopolyspora spinosa*, was recently discovered and was shown to exhibit excellent insecticidal activity. A83543 and each of the compounds are useful for the control of mites and insects, particularly Lepidoptera and Diptera species.

By "A83543 compounds" is meant components consisting of a 5,6,5-tricylic ring system, fused to a 12-membered macrocyclic lactone, a neutral sugar and an amino sugar (see Kirst et al. (1991), *Tetrahedron Letters*, 32:4839). The family of natural components of A83543 include a genus taught in EPO Application No. 0375316 and having the following general formula:

wherein $R^1$ is H or a group selected from

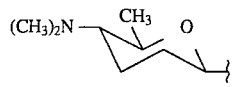 (a)

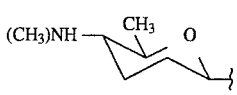 (b)

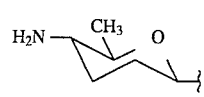 (c)

or)

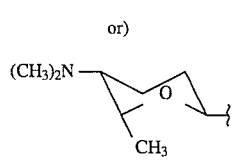 (d)

and $R^2$, $R^4$, $R_3$, $R^5$ and $R^6$ are hydrogen or methyl; or an acid addition salt thereof when $R^1$ is other than hydrogen.

The family of compounds from A83543 fermentation product has been shown to comprise individual components A83543A, A83543B, A83543C, A83543D, A83543E, A83543F, A83543G, A83543H and A83543J (see European Patent Publication No. O 375 316); and individual components A83543L, A83543M and A83543N (see copending U.S. patent application No. 07/790,287, filed Nov. 8, 1991). The structures of these individual components are shown below.

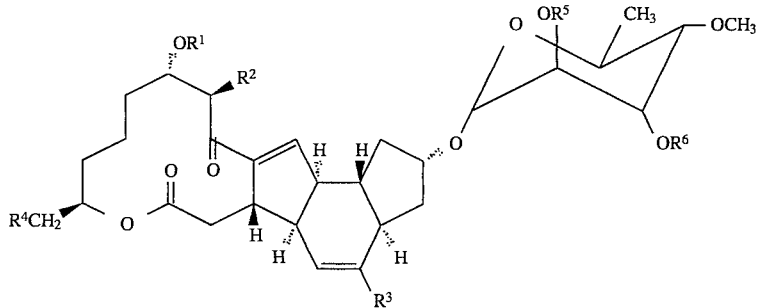

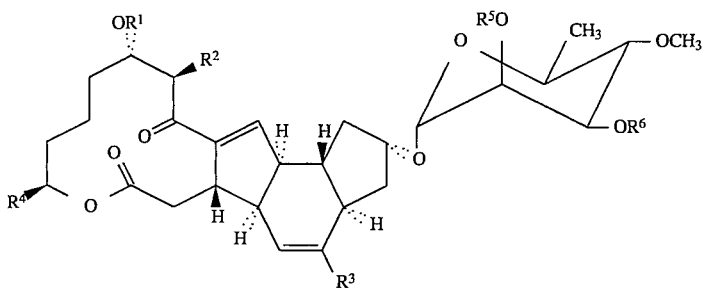

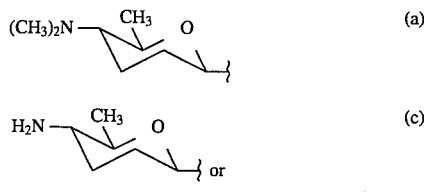
(a)

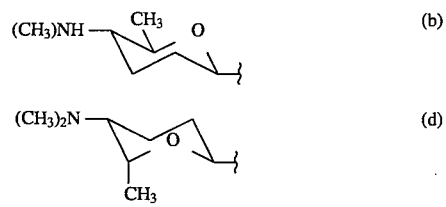
(b)

(c)

(d)

wherein $R^1$, $R^2$, $R^3$, $R^4$, $R^5$ and $R^6$ are for each component as follows:

| | Structures of A83543 Components | | | | | |
|---|---|---|---|---|---|---|
| Component | $R^1$ | $R^2$ | $R^3$ | $R^4$ | $R^5$ | $R^6$ |
| A | (a) | Me | H | Et | Me | Me |
| B | (b) | Me | H | Et | Me | Me |
| C | (c) | Me | H | Et | Me | Me |
| D | (a) | Me | Me | Et | Me | Me |
| E | (a) | Me | H | Me | Me | Me |
| F | (a) | H | H | Et | Me | Me |
| G | (d) | Me | H | Et | Me | Me |
| H | (a) | Me | H | Et | H | Me |
| J | (a) | Me | H | Et | Me | H |
| L | (a) | Me | Me | Et | Me | H |
| M | (b) | Me | H | Et | Me | H |
| N | (b) | Me | Me | Et | Me | H |
| PsaA1 | H | Me | H | Me | Me | Me |
| PsaD1 | H | Me | Me | Me | Me | Me |
| PsaE1 | H | Me | H | Me | Me | Me |
| PsaF1 | H | H | H | Me | Me | Me |
| PsaH1 | H | Me | H | Me | H | Me |
| PsaJ1 | H | Me | H | Me | Me | H |
| PsaL1 | H | Me | Me | Me | Me | H |

SUMMARY OF THE INVENTION

The present invention is directed to compounds of Formula 1:

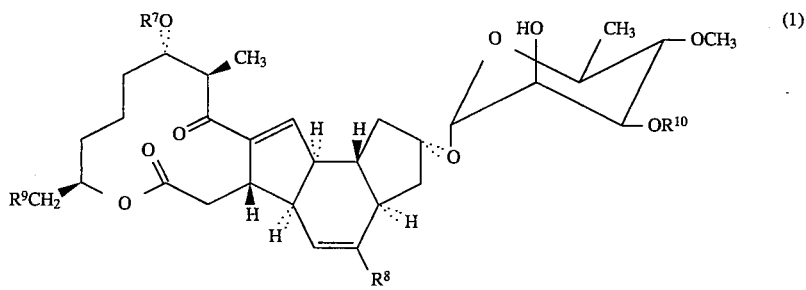

wherein $R^7$ is hydrogen or a group of formula

(a)

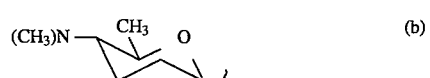
(b)

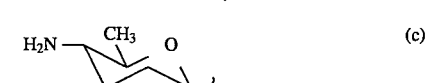
(c)

or

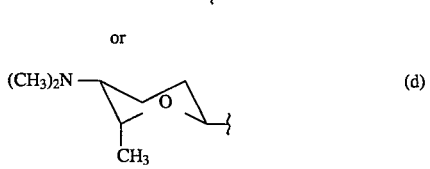
(d)

and $R^8$, $R^9$ and $R^{10}$ may independently be either hydrogen or methyl;
provided that when $R^7$ is

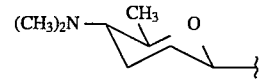

$R^8$ is hydrogen and $R^9$ and $R^{10}$ are not both methyl.

In particular, the present invention relates to new components of fermentation product A83543. The new components have been designated A83543Q, A83543R, A83543S and A83543T and compounds of Formula 1 wherein $R^7$, $R^8$, $R^9$ and $R^{10}$ are for each component as follows:

| Structures of A83543 Components | | | | |
|---|---|---|---|---|
| Component | $R^7$ | $R^8$ | $R^9$ | $R^{10}$ |
| Q | (a) | Me | Me | Me |
| R | (b) | H | Me | Me |
| S | (a) | H | H | Me |
| T | (a) | H | Me | H |

Another aspect of the present invention is a process for producing a compound of Formula 1, which comprises cultivating *S. spinosa* strain NRRL 18823 (A83543.9) or a Formula 1 compound producing mutant thereof, in a suitable culture medium, under submerged aerobic fermentation conditions, until a recoverable amount of a compound of Formula 1 is produced. The Formula 1 compound can be isolated and purified as described herein.

Because *S. spinosa* strain NRRL 18823 is a newly discovered strain, this invention further provides a biologically purified culture of this microorganism.

DETAILED DESCRIPTION OF THE INVENTION

This invention is directed to compounds that are new compounds of the family of related components produced by *S. spinosa*. The general structure of the compounds of the present invention is shown in the following formula:

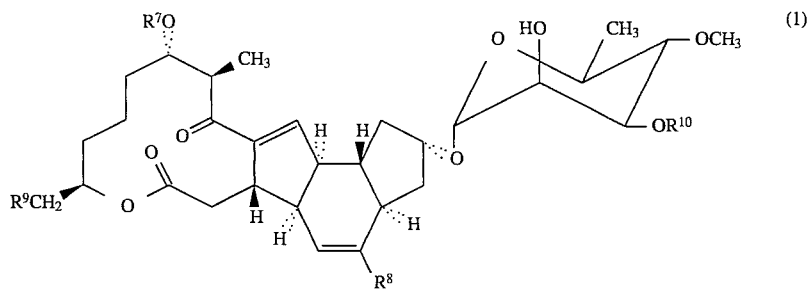

wherein $R^7$ is hydrogen or a group of formula

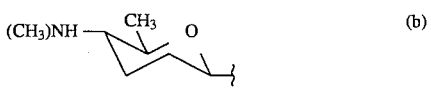

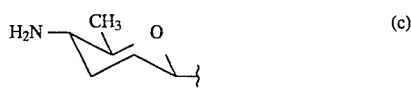

or

and $RS^8$, $R^9$ and $R^{10}$ may independently be either hydrogen or methyl;

provided that when $R^7$ is

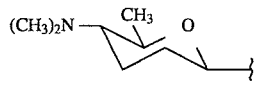

$R^8$ is hydrogen and $R^9$ and $R^{10}$ are not both methyl.

One aspect of the present invention is new components of fermentation product A83543. These new A83543 components, Formula 1 compounds, designated A83543Q, A83543R, A83543S and A83543T, wherein $R^7$, $R^8$, $R^9$ and $R^{10}$ are for each component as follows:

| Structures of A83543 Components | | | | |
|---|---|---|---|---|
| Component | $R^7$ | $R^8$ | $R^9$ | $R^{10}$ |
| Q | (a) | Me | Me | Me |
| R | (b) | H | Me | Me |
| S | (a) | H | H | Me |
| T | (a) | H | Me | H |

The chemical structures of the new components were determined by spectrometric methods, including infrared spectroscopy (IR), nuclear magnetic resonance spectroscopy (NMR), and ultraviolet spectroscopy (UV), and by comparison to the A83543 components (see Kirst, et al. (1991), supra). The following paragraphs describe the physical and spectral properties of components A83543Q, A83543R, A83543S and A83543T.

Figure 1:
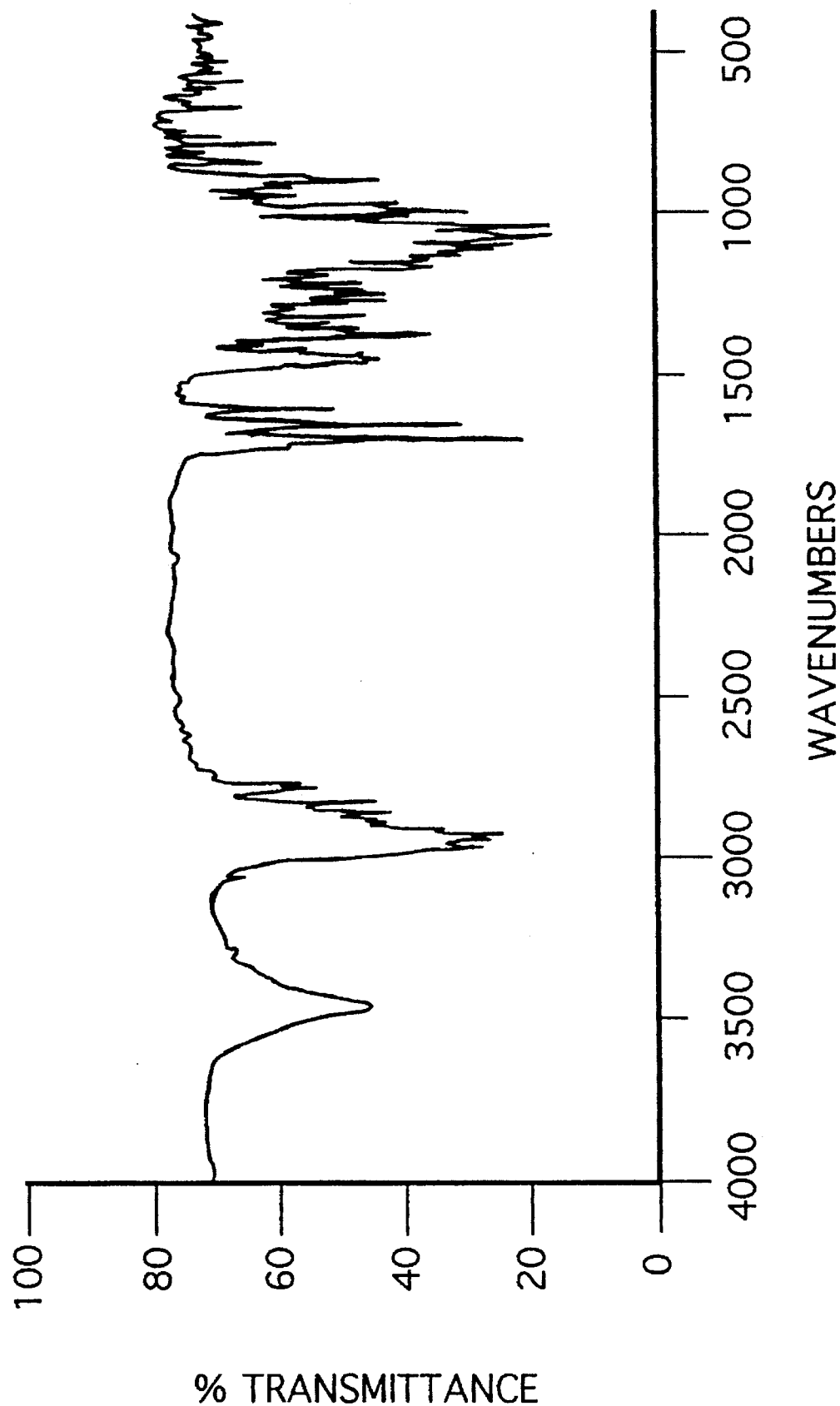
FIG. 1 shows the infrared absorption spectrum of A83543Q in KBr.

A83543Q:
A83543Q has the following characteristics:
Molecular weight: 731
Empirical formula: $C_{41}H_{65}NO_{10}$
UV (EtOH): 244 nm ($\epsilon=10,492$)
MS (FAB): (M+H) m/z 732
IR (KBR): see FIG. 1.

Figure 2:
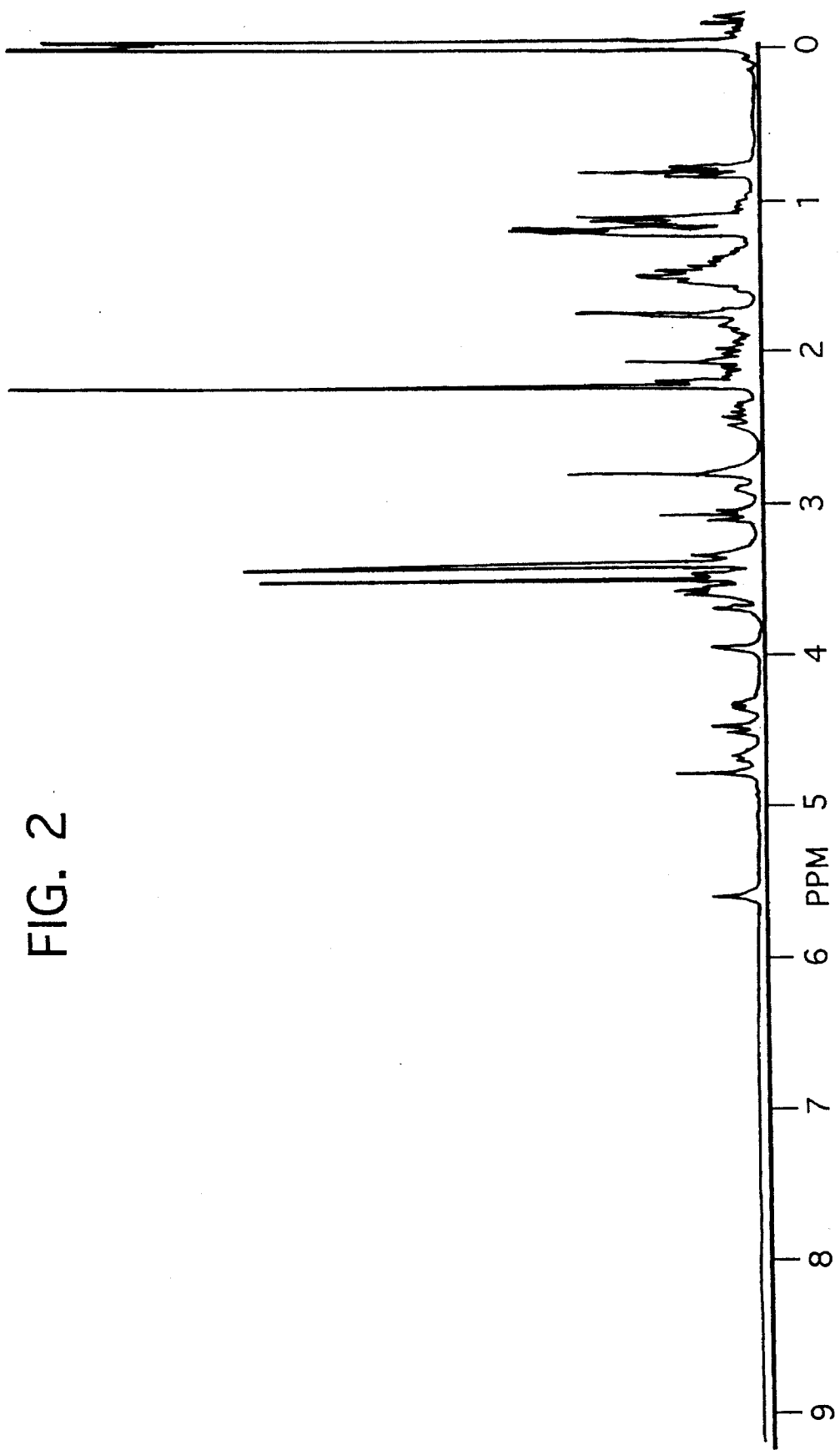
FIG. 2 shows the proton nuclear magnetic resonance spectrum of A83543Q in $d_6$-acetone.

Table I summarizes the $^1H$ and $^{13}C$ nuclear magnetic resonance (NMR) spectral data for A83543Q (in $d_6$-acetone), (see FIG. 2).

TABLE I

| $^1H$ and $^{13}C$ NMR data of A83543Q in acetone-$d_6$ | | |
|---|---|---|
| Position | $^{13}C$ | $^1H$* |
| 1 | 172.64 | — |
| 2 | 34.30 | 3.08/2.44 |
| 3 | 48.94 | 2.91 |
| 4 | 42.77 | 3.44 |
| 5 | 123.24 | 5.55 |
| 6 | 137.65 | — |
| 6-CH$_3$ | 20.82 | 1.74 |
| 7 | 45.32 | 2.18 |
| 8 | 35.47 | 2.00/1.45 |
| 9 | 76.35 | 4.32 |
| 10 | 38.52 | 2.36/1.39 |
| 11 | 46.96 | 1.05 |
| 12 | 49.98 | 2.79 |
| 13 | 148.53 | 7.04 |
| 14 | 145.12 | — |
| 15 | 203.12 | — |
| 16 | 48.44 | 3.31 |
| 17 | 80.88 | 3.53 |
| 18 | 35.05 | 1.50 |
| 19 | 22.53 | 1.81/1.18 |
| 20 | 30.87 | 1.53 |
| 21 | 76.84 | 4.65 |
| 22 | 29.12 | 1.48 |
| 23 | 9.53 | 0.81 |
| 24 | 16.24 | 1.12 |
| 1' | 99.51 | 4.75 |
| 2' | 68.44 | 3.94 |
| 3' | 82.52 | 3.33 |
| 4' | 82.62 | 3.06 |
| 5' | 68.33 | 3.55 |
| 6' | 18.19 | 1.20 |
| 3'-OCH$_3$ | 56.81 | 3.39 |
| 4'-OCH$_3$ | 60.71 | 3.46 |
| 1" | 104.06 | 4.47 |
| 2" | 31.90 | 1.94/1.39 |
| 3" | 18.72 | 1.81/1.49 |
| 4" | 65.98 | 2.12 |
| 5" | 74.05 | 3.56 |
| 6" | 19.39 | 1.21 |

TABLE I-continued

| $^1H$ and $^{13}C$ NMR data of A83543Q in acetone-$d_6$ | | |
|---|---|---|
| Position | $^{13}C$ | $^1H$* |
| N(CH$_3$)$_2$ | 40.95 | 2.21 |

*Values were taken from a heteronuclear one bond 2D correlation spectrum.

Figure 3:
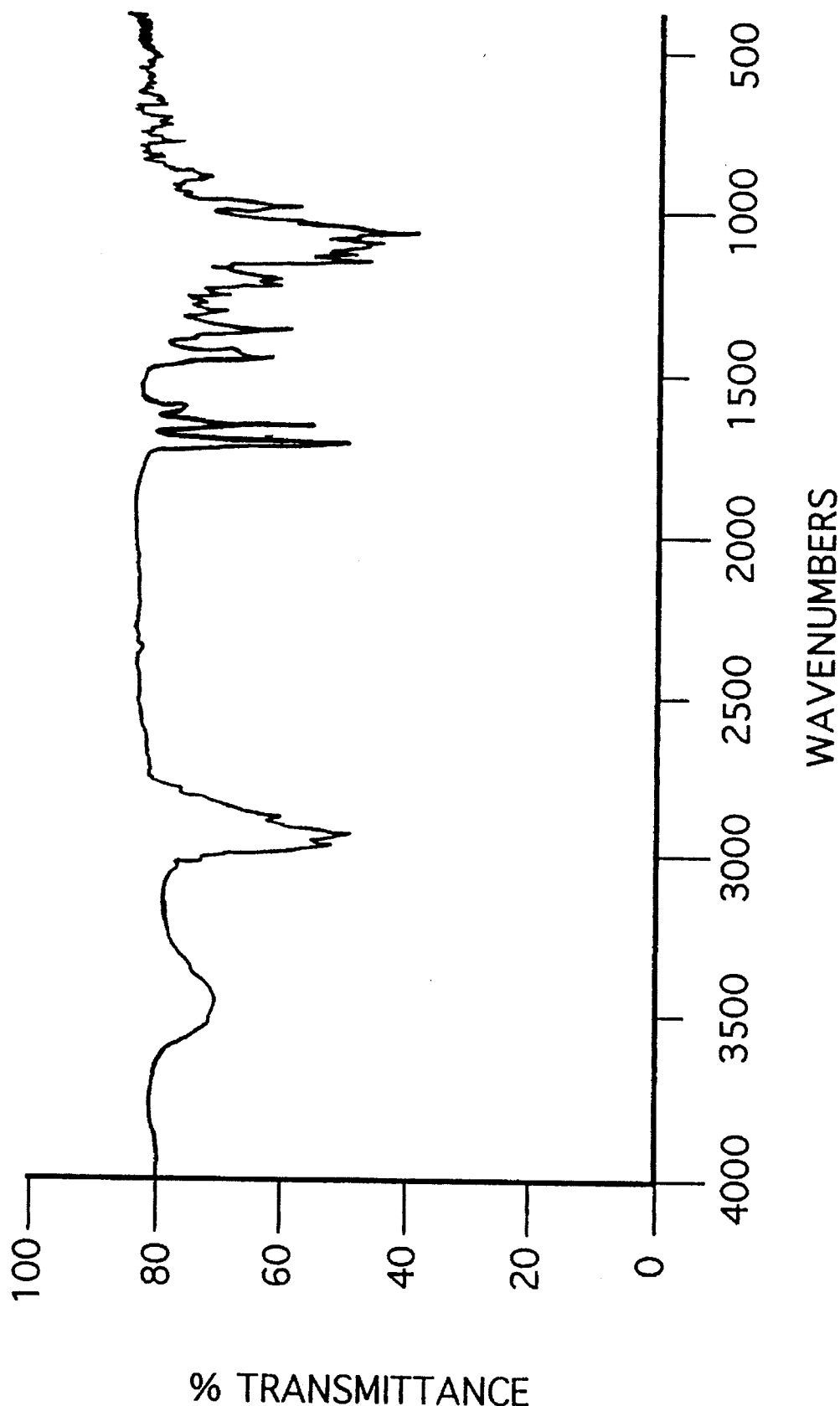
FIG. 3 shows the infrared absorption spectrum of A83543R in KBr.

A83543R:
A83543R has the following characteristics:
Molecular weight: 703
Empirical formula: $C_{39}H_{61}NO_{10}$
UV (EtOH): 245 nm ($\epsilon=10,991$)
MS (FAB): (M+H) m/z 704
IR (KBR): (see FIG. 3).

Figure 4:
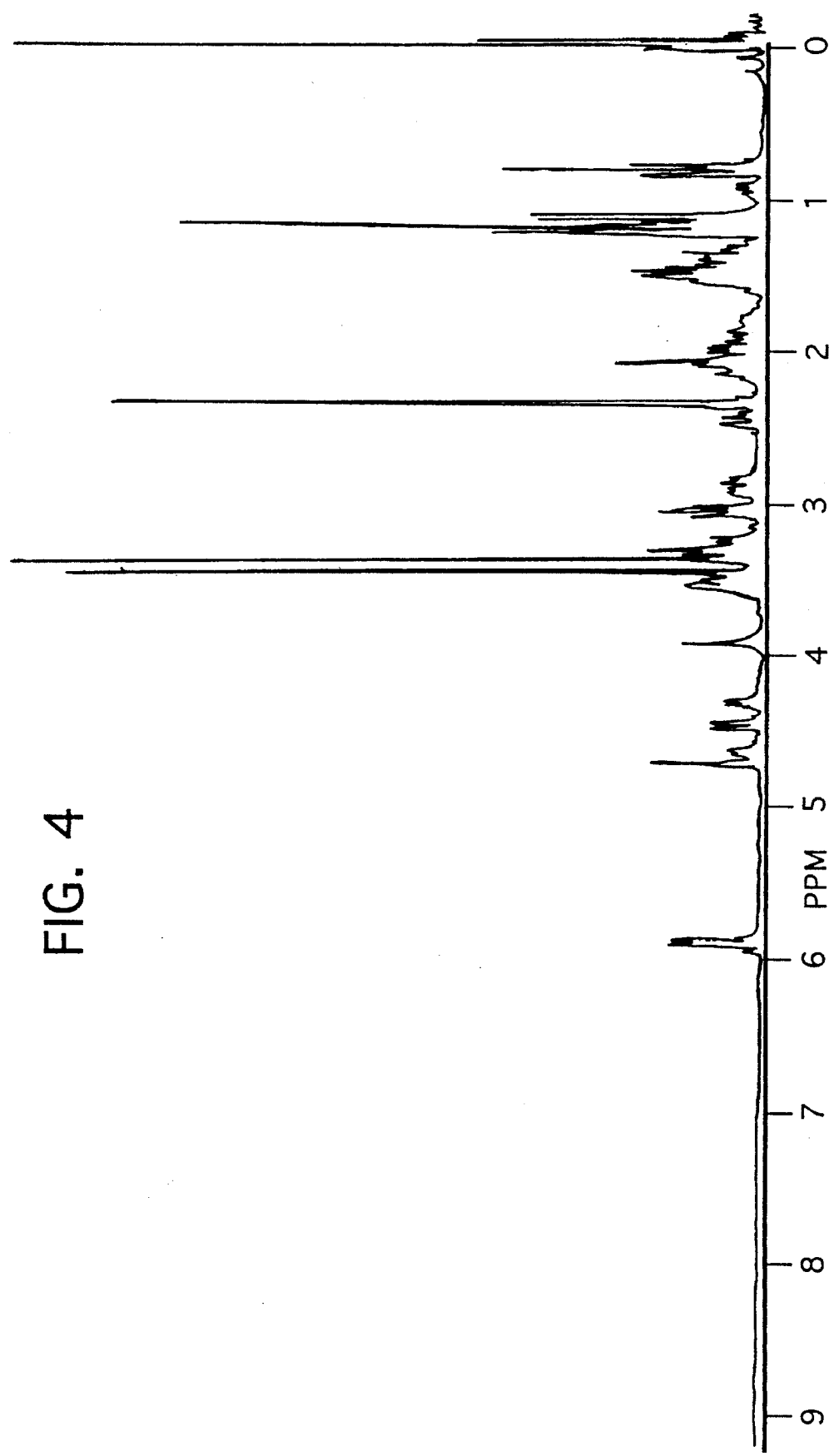
FIG. 4 shows the proton nuclear magnetic resonance spectrum of A83543R in $d_6$-acetone.

Table II summarizes the $^1H$ and $^{13}C$ nuclear magnetic resonance (NMR) spectral data for A83453R (in acetone-$d_6$) (see FIG. 4).

TABLE II

| $^1H$ and $^{13}C$ NMR data of A83543R in acetone-$d_6$ | | |
|---|---|---|
| Position | $^{13}C$ | $^1H$* |
| 1 | 172.63 | — |
| 2 | 34.41 | 30.8/2.46 |
| 3 | 48.71 | 2.95 |
| 4 | 42.23 | 3.51 |
| 5 | 129.67 | 5.87 |
| 6 | 130.29 | 5.91 |
| 7 | 42.04 | 2.16 |
| 8 | 37.02 | 1.95/1.36 |
| 9 | 76.64 | 4.33 |
| 10 | 38.19 | 2.37/1.38 |
| 11 | 47.01 | 0.93 |
| 12 | 50.33 | 2.87 |
| 13 | 148.43 | 7.06 |
| 14 | 144.84 | — |
| 15 | 203.08 | — |
| 16 | 48.32 | 3.31 |
| 17 | 80.99 | 3.56 |
| 18 | 35.06 | 1.52 |
| 19 | 22.41 | 1.79/1.19 |
| 20 | 30.91 | 1.59/1.46 |
| 21 | 76.83 | 4.66 |
| 22 | 29.06 | 1.48 |
| 23 | 9.55 | 0.81 |
| 24 | 16.31 | 1.13 |
| 1' | 99.51 | 4.74 |
| 2' | 68.31 | 3.93 |
| 3' | 82.48 | 3.33 |
| 4' | 82.59 | 3.07 |
| 5' | 68.31 | 3.53 |
| 6' | 18.18 | 1.19 |
| 3'-OCH$_3$ | 56.80 | 3.39 |
| 4'-OCH$_3$ | 60.70 | 3.47 |
| 1" | 104.16 | 4.48 |
| 2" | 31.70 | 1.88/1.42 |
| 3" | 29.06 | 2.11/1.23 |
| 4" | 61.82 | 1.98 |
| 5" | 76.52 | 3.26 |
| 6" | 19.30 | 1.22 |
| NHCH$_3$ | 34.18 | 2.35 |

*Values were taken from a heteronuclear one bond 2D correlation spectrum.

Figure 5:
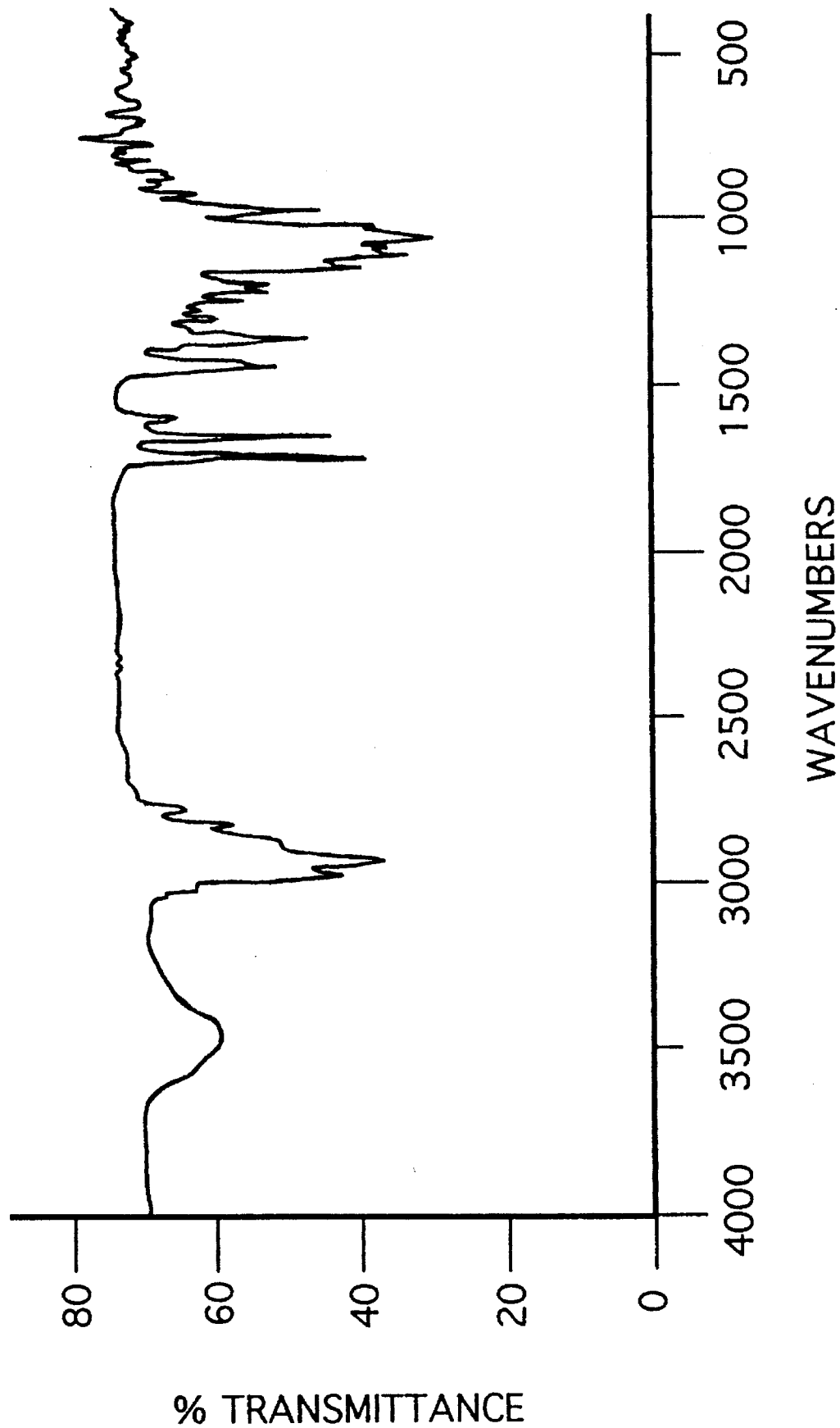
FIG. 5 shows the infrared absorption spectrum of A83543S in KBr.

A83543S:
A83543S has the following characteristics:
Molecular weight: 703
Empirical formula: $C_{39}H_{61}NO_{10}$
UV (EtOH): 244 nm ($\epsilon=9,697$)
MS (FAB): (M+H) m/z 704
IR (KBR): see FIG. 5.

Figure 6:
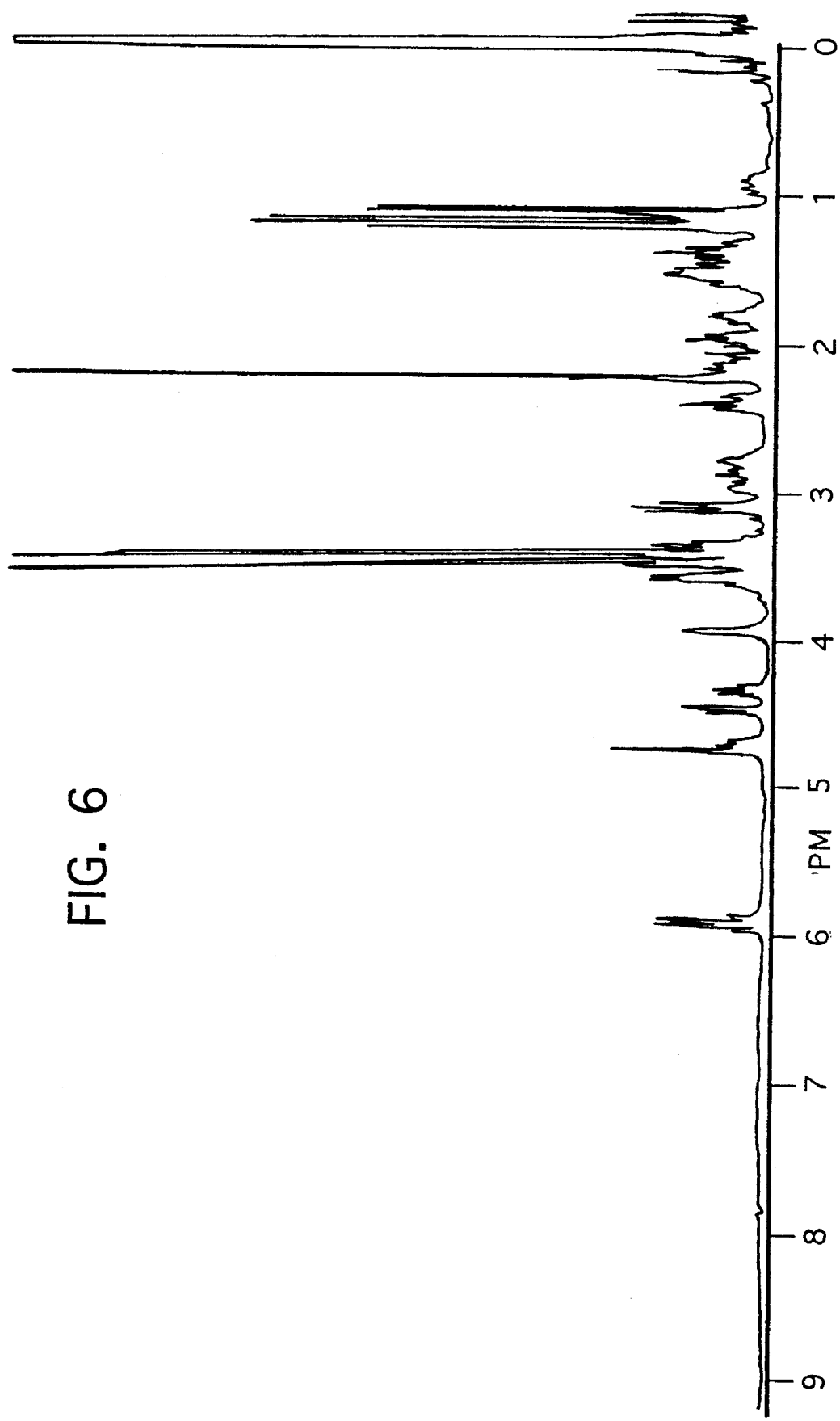
FIG. 6 shows the proton nuclear magnetic resonance spectrum of A83543S in $d_6$-acetone.

Table III summarizes the $^1$H and $^{13}$C nuclear magnetic resonance (NMR) spectral data for A83454S (in acetone-$d_6$) (see FIG. 6).

TABLE III $^1$H and $^{13}$C NMR data of A83543S in acetone-$d_6$

| Position | $^{13}$C | $^1$H* |
|---|---|---|
| 1 | 172.39 | — |
| 2 | 34.86 | 3.06/2.40 |
| 3 | 48.79 | 2.95 |
| 4 | 42.03 | 3.43 |
| 5 | 129.66 | 5.86 |
| 6 | 130.32 | 5.91 |
| 7 | 41.99 | 2.16 |
| 8 | 37.04 | 1.97/1.38 |
| 9 | 76.65 | 4.33 |
| 10 | 38.20 | 2.35/1.38 |
| 11 | 47.08 | 0.93 |
| 12 | 50.31 | 2.86 |
| 13 | 148.37 | 7.05 |
| 14 | 144.74 | — |
| 15 | 203.01 | — |
| 16 | 47.98 | 3.34 |
| 17 | 81.16 | 3.56 |
| 18 | 34.90 | 1.61/1.52 |
| 19 | 22.25 | 1.80/1.17 |
| 20 | 33.57 | 1.50 |
| 21 | 72.97 | 4.68 |
| 22 | 21.62 | 1.12 |
| 24 | 16.44 | 1.13 |
| 1' | 99.51 | 4.73 |
| 2' | 68.41 | 3.93 |
| 3' | 82.51 | 3.33 |
| 4' | 82.59 | 3.06 |
| 5' | 68.31 | 3.53 |
| 6' | 18.19 | 1.19 |
| 3'-OCH$_3$ | 56.81 | 3.38 |
| 4'-OCH$_3$ | 60.71 | 3.47 |
| 1" | 104.05 | 4.47 |
| 2" | 31.92 | 1.94/1.41 |
| 3" | 18.71 | 1.83/1.52 |
| 4" | 65.95 | 2.13 |
| 5" | 74.03 | 3.56 |
| 6" | 19.39 | 1.21 |
| N(CH$_3$)$_2$ | 40.96 | 2.21 |

*Values were taken from a heteronuclear one bond 2D correlation spectrum.

A83543T:

A83543T has the following characteristics:

Molecular weight: 703

Empirical formula: $C_{39}H_{61}NO_{10}$

UV (EtOH): 245 nm ($\epsilon$=13,082)

MS (FAB): (M+H) m/z 704

Figure 7:
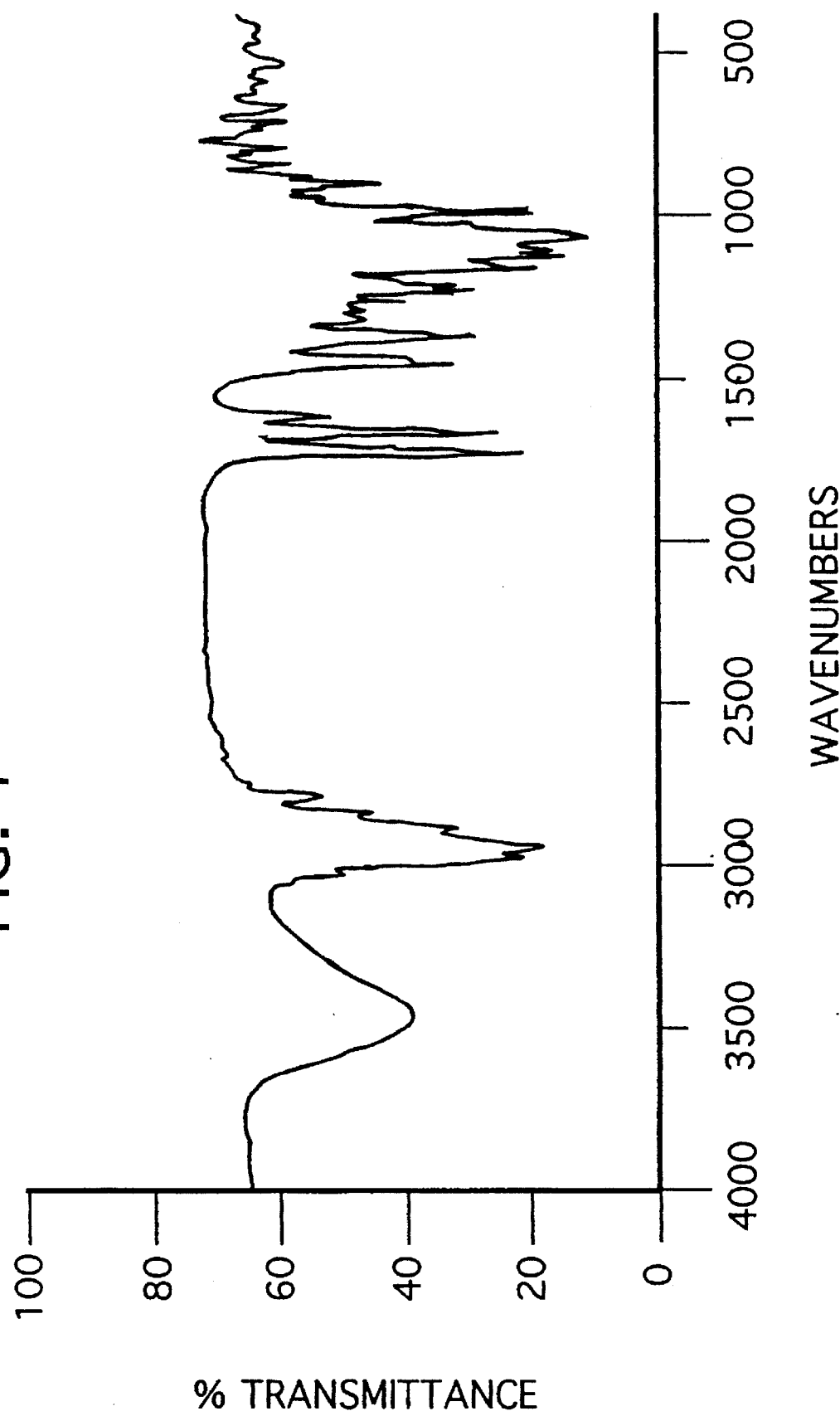
FIG. 7 shows the infrared absorption spectrum of A83543T in KBr.

IR (KBR): see FIG. 7.

Figure 8:
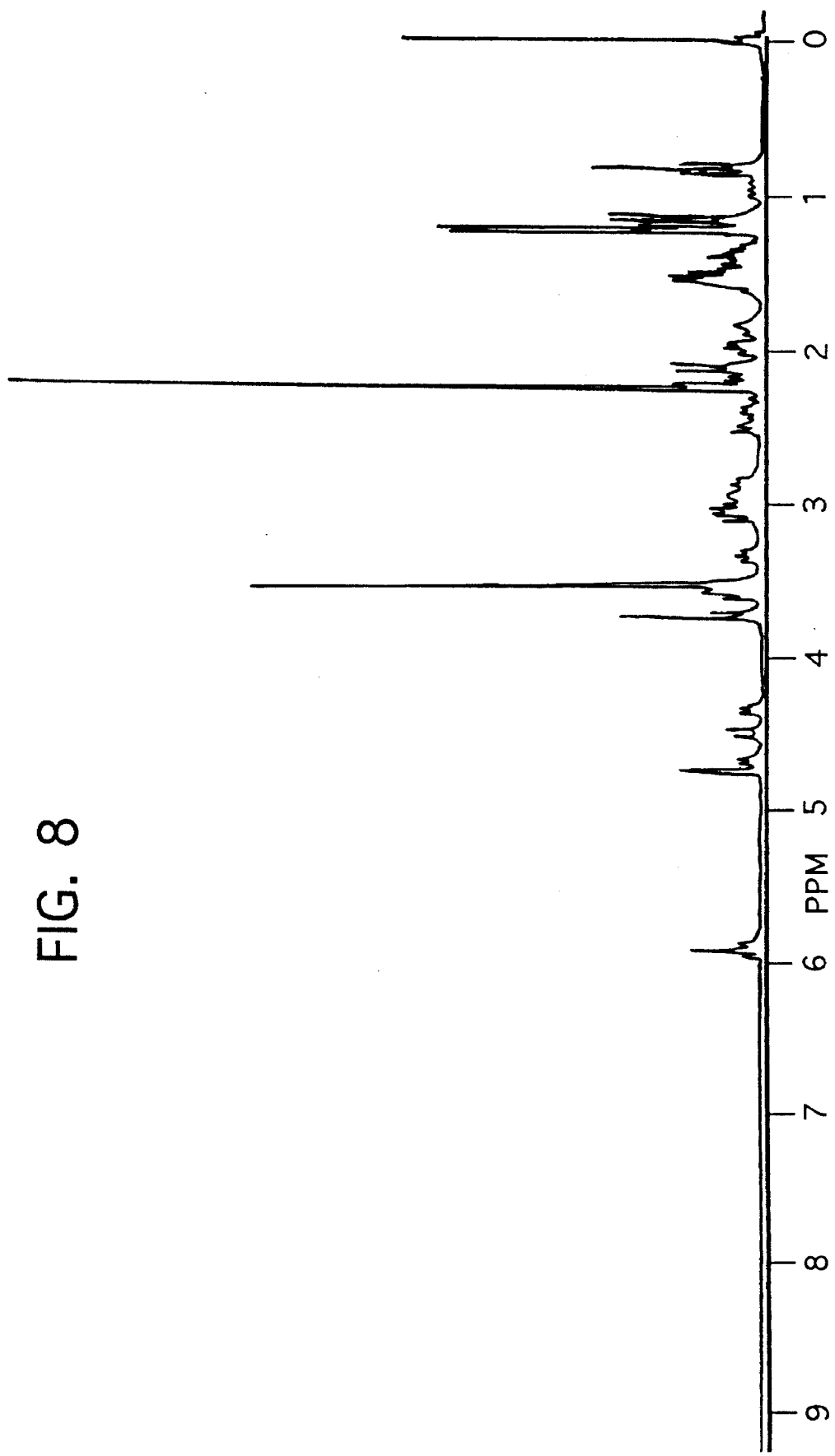
FIG. 8 shows the proton nuclear magnetic resonance spectrum of A83543T in $d_6$-acetone.

Table IV summarizes the $^1$H and $^{13}$C nuclear magnetic resonance (NMR) spectral data for A83454T (in acetone-$d_6$) (see FIG. 8).

TABLE IV $^1$H and $^{13}$C NMR data of A83543T in acetone-$d_6$

| Position | $^{13}$C* | $^1$H* |
|---|---|---|
| 1 | 172.65 | — |
| 2 | 34.25 | 3.11/2.49 |
| 3 | 48.50 | 2.97 |
| 4 | 41.92 | 3.54 |
| 5 | 129.69 | 5.91 |
| 6 | 130.31 | 5.94 |
| 7 | 42.01 | 2.18 |
| 8 | 37.03 | 1.98/1.39 |
| 9 | 76.44 | 4.36 |
| 10 | 38.18 | 2.39/1.39 |
| 11 | 47.32 | 0.96 |
| 12 | 50.14 | 2.89 |
| 13 | 148.36 | 7.09 |
| 14 | 144.85 | — |
| 15 | 203.12 | — |
| 16 | 48.22 | 3.35 |
| 17 | 80.83 | 3.57 |
| 18 | 34.99 | 1.57/1.51 |
| 19 | 22.34 | 1.82/1.22 |
| 20 | 30.83 | 1.58/1.49 |
| 21 | 76.72 | 4.69 |
| 22 | 29.04 | 1.52 |
| 23 | 9.29 | 0.84 |
| 24 | 16.14 | 1.16 |
| 1' | 99.46 | 4.75 |
| 2' | 72.61 | 3.71 |
| 3' | 72.61 | 3.69 |
| 4' | 84.12 | 3.05 |
| 5' | 68.22 | 3.57 |
| 6' | 18.18 | 1.24 |
| 4'-OCH$_3$ | 60.55 | 3.60 |
| 1" | 104.55 | 4.50 |
| 2" | 31.81 | 1.97/1.43 |
| 3" | 18.59 | 1.86/1.55 |
| 4" | 65.76 | 2.15 |
| 5" | 73.98 | 3.60 |
| 6" | 19.24 | 1.24 |
| N(CH$_3$)$_2$ | 40.95 | 2.25 |

*Values were taken from 1D or inverse 2D one bond configuration.

The term "new A83543 component" means a compound selected from the compounds of Formula 1, including A83543Q, A83543R, A83543S and A83543T.

Additioanlly, the amino sugar can be selectively removed from the Formula 2 compounds to give corresponding pseudoaglycones, termed Formula 3 compounds. These compounds are a further aspect of the present invention and are the compounds of Formula 1 wherein $R^1$ is hydrogen.

The selective removal of the amino sugar from A83543Q, A83543R, A83543S and A83543T produces A83543Q pseudoaglycone, A83543H pseudoaglycone, A83543S pseudoaglycone and A83543T pseudoaglycone, respectively. These compounds are shown in the following formula:

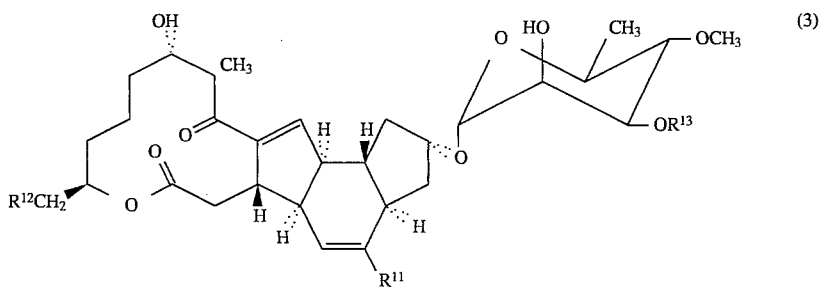

(3)

wherein $R^{11}$, $R^{12}$ and $R^{13}$ are for each component as follows:

Structures of A83543 Components

| Component | $R^{11}$ | $R^{12}$ | $R^{13}$ |
|---|---|---|---|
| pseudoaglycone Q | Me | Me | Me |
| pseudoaglycone H | H | Me | Me |
| pseudoaglycone S | H | H | Me |
| pseudoaglycone T | H | Me | H |

The Formula 2 compounds are used to prepare the pseudoaglycones by the reaction of a Formula 2 compound with acid to remove the amino sugar. Suitable acids include hydrochloric and sulfuric, the preferred acid for the transformation is sulfuric. The reaction is preferably carried out in a polar organic solvent, a mixture of a polar organic solvent and water, or water. Suitable organic solvents include methanol, THF, acetonitrile and dioxane. The preferred solvents for the transformation are a mixture of methanol and water or water. The reaction may be carried out at a temperature from about 25° C. to about 95° C., preferably at 80° C.

The pseudoaglycones are useful as starting materials for the preparation of new A83543 compounds, for example, the pseudoaglycone may be glycosylated at the hydroxyl group where the amino sugar was present. This glycosylation may be carried out by chemical synthesis or by microbial bioconversion.

Another aspect of the present invention is the chemical demethylation of certain Formula 1 compounds. The Formula 1 compounds may be grouped into 3 non-inclusive subgroups: 1A, 1B, and 1C. The Formula 1A compounds are the Formula 1 compounds wherein $R^7$ is a group of formula:

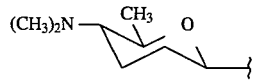

The Formula 1B compounds are the Formula 1 compounds wherein $R^7$ is a group of formula:

The Formula 1C compounds are the Formula 1 compounds wherein $R^7$ is a group of formula:

As described herein, the Formula 1B compounds may be prepared from the Formula 1A compounds. Similarly, the Formula 1C compounds may be prepared from the Formula 1A compounds and Formula 1B compounds. These compounds may be prepared by chemical demethylation of a corresponding new A83543 component. Each of these subgroups is also a subset of the Formula 2 compounds.

The N-demethyl derivatives, the Formula 1B compounds, are prepared by the reaction of a Formula 1A compound with iodine. The reaction is carried out in a polar organic solvent, such as methanol, or a mixture of a polar organic solvent and water, such as aqueous methanol. When the reaction is carried out in aqueous methanol, a buffer may be added to the solvent mixture. A preferred buffer is sodium acetate. The reaction is preferably carried out at a temperature from about 30° C. to about 70° C. for about 2 to about 6 hours.

The di-N-demethyl derivatives, the Formula 1C compounds, may be prepared by the reaction of a Formula 1A and 1B compound with sodium methoxide/iodine. The reaction is preferably carried out in a polar organic solvent, such as methanol. Further, the reaction is carried out at a temperature from about −10° C. to about 15° C., preferably between 0° C. to 5° C. The reaction times vary from about 4 hours to about 6 hours.

Illustrative examples of the Formula 1B and 1C compounds are shown in the following formula:

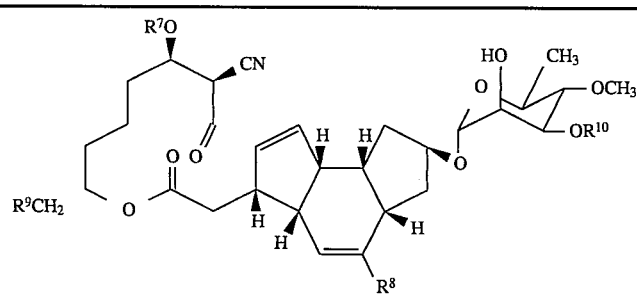

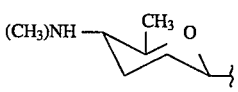

(b)

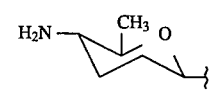

(c)

| Compound | $R^7$ | $R^8$ | $R^9$ | $R^{10}$ |
|---|---|---|---|---|
| N-demethyl-A83543Q | (b) | $CH_3$ | $CH_3$ | $CH_3$ |
| di-N-demethyl-A83543Q | (c) | $CH_3$ | $CH_3$ | $CH_3$ |
| N-demethyl-A83543R | (c) | H | $CH_3$ | $CH_3$ |
| N-demethyl-A83543S | (b) | H | H | $CH_3$ |
| di-N-demethyl-A83543S | (c) | H | H | $CH_3$ |
| N-demethyl-A83543T | (b) | H | $CH_3$ | H |
| di-N-demethyl-A83543T | (c) | H | $CH_3$ | H |

The Formula 2 compounds, which are the Formula 1 compounds wherein $R^7$ is other than hydrogen, can react to form various salts, which are also a part of this invention. These salts are useful, for example, in separating and purifying the Formula 2 compounds. In addition, some of the salt forms may have increased water solubility. These salts are prepared using standard procedures for salt preparation. For example, A83543Q can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maelic, fumaric, cholic, pamoic, mucic, glutamic, camphoric, glutaric, glycolic, phthalic, tartaric, formic, lauric, stearic, salicyclic, methanesulfonic, benzenesulfonic, sorbic, picric, benzoic, cinnamic, and like acids.

The Formula 2 compounds are generally produced by culturing an A83543-producing strain of *S. spinosa* sp. nov. under submerged aerobic conditions in a suitable culture medium, until a recoverable amount of the Formula 2 compound is produced. The Formula 2 compound can be recovered using various isolation and purification procedures which are understood in the art.

For convenience in the discussions which follow, A83543A-producing strains have been given the following designations: A83543.1 and A83543.4 were used to prepare a new A83543Q-producing strain, designated A83543.9. Cultures A83543.1, A83543.4 and A83543.9 have been deposited and made a part of the stock culture collection of the Midwest Area Regional Research Center, Agricultural Research Service, U.S. Department of Agriculture, from which they are available to the public under the following accession numbers:

| NRRL No. | Strain No. |
|---|---|
| 18395 | A83543.1 |
| 18538 | A83543.4 |
| 18823 | A83543.9 |

Culture A83543.1 was obtained by chemical mutation of culture A83543, which was isolated from a soil sample collected in the Virgin Islands. Mertz and Yao (1990), *Int'l J. of Systematic Bacteriology*, 40:34. Cultures 83543.4 were all derived from culture A83543.1. Culture A83543.9 was derived from A83543.4 by chemically-induced mutagenesis with N-methyl-N'-nitro-N-nitrosoguanidine. The following data show that these distinct isolates are all strains of *S. spinosa* and have very few cultural, morphological or biochemical differences. Except for =differences in the production of the A83543 components, these isolates appear similar to the parent culture.

CULTURAL CHARACTERISTICS

Cultures A83543.1, A83543.4, and A83543.9 were grown on twelve agar plating media and compared for growth, reverse color, aerial hyphae production, spore mass color, and soluble pigment production. No significant differences were observed on any of the media used. The cultures grew well on both complex and defined media. Aerial hyphae were produced on most of the media used. The aerial spore mass color was predominantly white, and the reverse side was yellow to yellow-brown. No distinctive pigmentation was present; however, a soluble brown pigment was released into some media. These cultural characteristics are the same as presented in the original taxonomic description of A83543.1 (see Mertz and Yao (1990), supra).

MORPHOLOGICAL CHARACTERISTICS

No significant differences were observed between any of the strains compared. Well-formed aerial hyphae, which were segmented into long chains of spores arranged as hooks and open loops, were present on most of the media. Spirals were also observed, but they were short and incomplete. The general morphology was rectus-flexibilis. Aerial hyphae of each of the strains had a distinctive bead-like appearance, with many empty spaces in the spore chain. This feature demonstrated that a spore sheath encased the spore chain, which is a distinctive feature of the genus Saccharopolyspora.

PHYSIOLOGICAL CHARACTERISTICS

Fatty acid analyses from each of the strains were compared. Cells were grown for 96 hours at 28° C. in trypticase soy broth (Difco Laboratories, Detroit, Mich.). Fatty acid methyl esters were analyzed by gas-liquid chromatography with a model 5898A computer-controlled gas-liquid chromatography system (Hewlett-Packard Co., Palo Alto, Calif.) (see Miller and Berger, "Bacterial Identification by Gas Chromatography of Whole Cell Fatty Acids," Hewlett-Packard Application Note 228-41. These results are presented in Table IV).

TABLE IV

| Percentage Fatty Acid Composition of A83543 Strains | | | |
|---|---|---|---|
| Fatty Acid | A83543.1 | A83543.4 | A83543.9 |
| 15:0 ISO | 15.95 | 22.47 | 17.42 |
| 16:0 ISO | 28.71 | 22.00 | 24.34 |
| 16:1 Cis 9 | — | 1.35 | 0.92 |
| 15:0 ISO 2OH | 2.67 | 2.02 | 1.78 |
| 16:0 | 1.20 | 0.69 | 0.36 |
| 17:1 ISO F[1] | 5.52 | 8.62 | 8.72 |
| 17:0 Iso | 13.55 | 20.67 | 19.43 |
| 17:0 Anteiso | 8.39 | 3.94 | 5.52 |
| 17:1 B | 4.14 | 3.97 | 4.61 |
| 17:1 C | 2.52 | 2.88 | 3.02 |
| 17:0 | 4.26 | 1.49 | 1.67 |
| 16:1 2OH | 1.87 | 1.52 | 2.17 |
| 18:1 Iso F | 6.55 | 4.16 | 5.74 |
| 18:1 Cis 9 | 0.34 | 1.03 | 0.84 |

[1]F, B, and C indicate double bond positions or configurations that are unknown.

Figure 9:
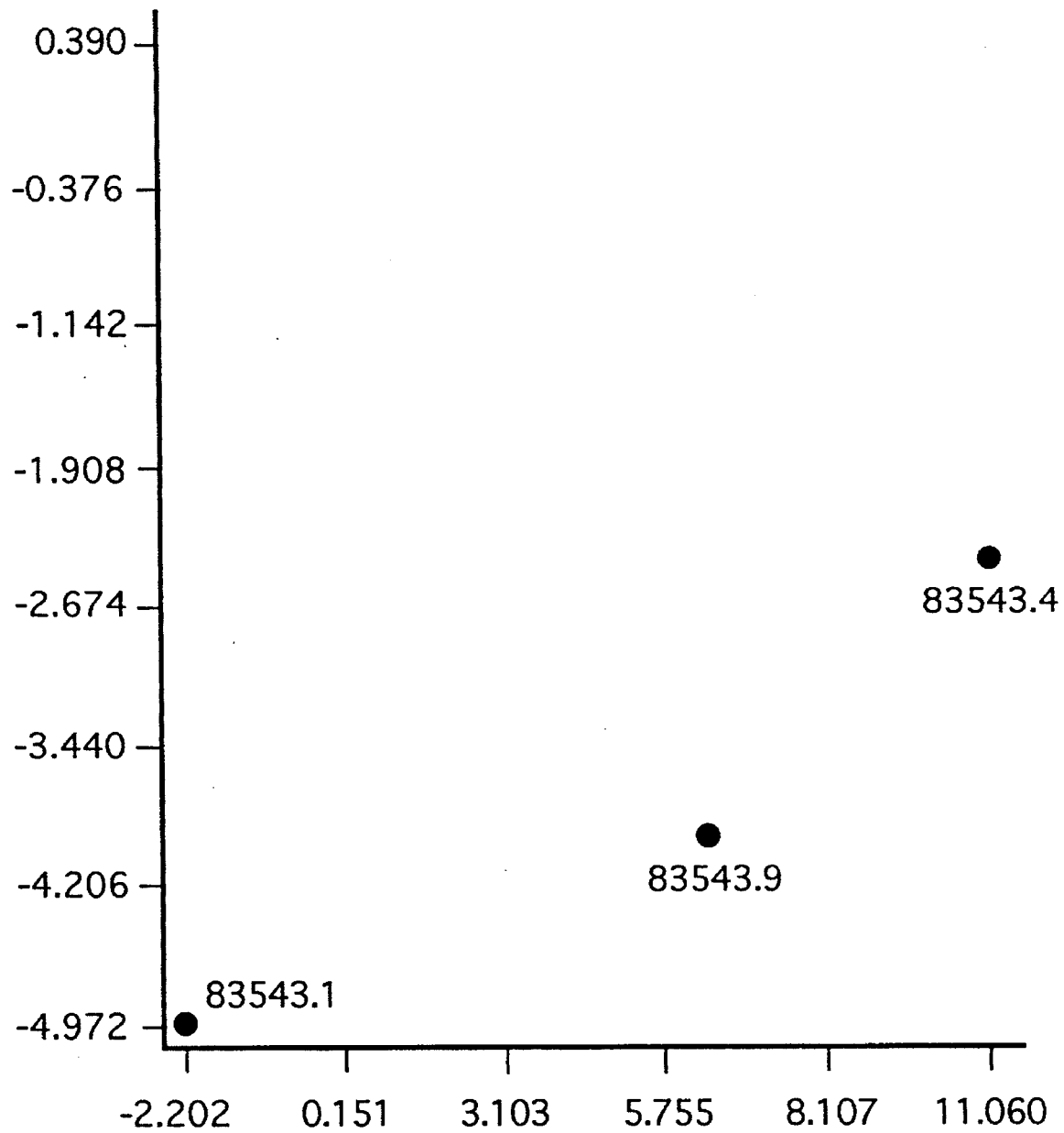
FIG. 9 shows the principle component plot of fatty acid analyses for strains A83543.1, A83543.4 and A83543.9.

Principal-component analysis is a branch of multivariate statistics that deals with internal relationships of a set of variables. In this analysis, the greatest amount of variance within the original data or test results is expressed as principal components (see Alderson, "The Application and Relevance of Nonheirarchic Methods in Bacterial Taxonomy", in *Computer-Assisted Bacterial Systematics* 227 (1985)). A plot showing scatter or variability can be constructed. Relationships can be evaluated by examining the variance, and a microbial population characterized. A two-dimensional principal component plot from the fatty acid analyses of strains A83543.1, A83543.4 and A83543.9 is shown in FIG. 9. The values refer to the degrees of separation between the strains involved. The differences between the strains represent strain differences.

As is the case with other organisms, the characteristics of the A83543Q-producing strains are subject to variation. Thus, mutants of these strains may be obtained by physical and chemical methods known in the art. For example, other strains may be obtained by treatment with chemicals such as N-methyl-N'-nitro-N-nitrosoguanidine. Natural and induced mutants of the *S. spinosa* NRRL 18823 strains, which retain the characteristic of producing recoverable amounts of a Formula 2 compound are applicable in the present invention.

One aspect of the present invention is the production of a compound of Formula 2 by culturing *S. spinosa* strain NRRL 18823, or an A83543Q-producing mutant thereof, in a suitable culture medium. An "A83543Q-producing mutant" is a stirain derived from *S. spinosa* NRRL 18823 which is capable of producing recoverable amounts of A83543Q. Strain NRRL 18823 produces A83543 components containing α-3,4-di-O-methylrhamnose. The biosynthetic mechanism for methylating the 2-hydroxy group of rhamnose is defective in this new strain. After production, the Formula 2 compound may be separated from the culture medium using various isolation and purification procedures which are well understood in the art.

For economy in production, optimal yield, and ease of product isolation, certain culture media are preferred. For example, preferred carbon sources in large-scale fermentation are glucose and methyl oleate, although ribose, xylose, fructose, galactose, mannose, mannitol, soluble starch, potato dextrin, oils such as soybean oil and the like can also be used. Preferred nitrogen sources are cottonseed flour, peptonized milk and corn steep liquor, although fish meal, digested soybean meal, yeast extract, enzyme-hydrolyzed casein, beef extract, and the like can also be used. Among the nutrient inorganic salts which can be incorporated in the culture media are theicustomary soluble salts capable of yielding zinc, sodium, magnesium, calcium, ammonium, chloride, carbonate, sulfate, nitrate and like ions. Essential trace elements necessary for the growth and development of the organism should also be included in the culture medium. Such trace elements commonly occur as impurities in other substituents of the medium in amounts sufficient to meet the growth requirements of the organism.

Usually, if foaming is a problem, small amounts (i.e., 0.2 ml/L) of an antifoam agent such as polypropylene glycol may be added to large-scale fermentation media. In the case of the A83543-producing cultures, however, conventional defoamers inhibit A83543 production. Foaming can be controlled by including soybean oil or PLURONIC L-101 (BASF, Parsipanny, N.J.) in the medium (1–3%). Additional oil may be added if foaming develops.

For production of substantial quantities of a Formula 2 compound, submerged aerobic fermentation in stirred bioreactors is preferred; however, small quantities of a Formula 2icompound may be obtained by shake-flask culture. Because of the time lag in production commonly associated with inoculation of large bioreactors with the spore form of the organism, it is preferable to use a vegetative inoculum. The vegetative inoculum is prepared by inoculating a small volume of culture medium from a stock culture preserved in liquid nitrogen to obtain a fresh, actively growing culture of the organism. The vegetative inoculum is then transferred to a larger bioreactor. The vegetative inoculum medium can be the same as that used for larger fermentations, but other media are also suitable.

The Formula 2 compounds are produced by the A83543Q-producing strains when grown at temperatures between about 24° and about 33° C. Optimum temperatures for production appear to be about 28°–30° C.

As is customary in submerged aerobic culture processes, sterile air is blown into the vessel from the bottom while the medium is stirred with conventional turbine impellors. In general, the aeration rate and agitation rate should be sufficient to maintain the level of dissolved oxygen at or above 80% of air saturation, preferably above 70%, with an internal vessel pressure of about 0.34 atmospheres.

Production of A83543Q, A83543R, A83543S or A83543T can be followed during the fermentation by testing extracts of the broth. A preferred method for following the production is analysis of the broth extracts by high performance liquid chromatography (HPLC). A suitable system for analysis is described in Example 1.

Following the production in shake flasks or in stirred reactors, the Formula 2 compound can be recovered from the fermentation medium by methods used in the art. The compounds produced during fermentation of the A83543Q-producing strain occur in both the mycelia and the broth. The Formula 2 compounds are lipophilic; when a substantial amount of oil is used in the fermentation, whole broth extraction is more efficient. If only small amounts of oil are used, the major portion of the Formula 2 compound is present in the mycelia. In that case, more efficient recovery of the Formula 2 compound is accomplished by initially filtering the medium to separate the broth from the mycelial mass (the biomass).

The Formula 2 compound can be recovered from the biomass by a variety of techniques. A suitable technique involves washing the separated biomass with water to remove remaining broth, mixing the biomass with a polar solvent in which the Formula 2 compound is soluble, e.g. methanol or acetone, separating and concentrating the solvent, extracting the concentrate with a non-polar solvent and/or adsorbing it onto a reverse-phase silica gel adsorbent, such as reverse phase $C_8$ or $C_{18}$ resin, or a high porous polymer such as HP-20 or HP-20SS (Mitsubishi Chemical Industries Co., Ltd., Japan). The active material is eluted from the adsorbent with a suitable solvent such as, for example, acetonitrile:methanol mixtures, optionally containing small amounts of THF.

A preferred technique for isolating the Formula 2 compound from the biomass involves adding an equal volume of acetone to the whole broth, filtering the mixture in a ceramic filter to remove the biomass, and extracting the filtrate with ethyl acetate. The ethyl acetate extract is concentrated invacuo to remove the acetone, and the aqueous layer is separated from the organic layer. The ethyl acetate solution is further concentrated in vacuo, and the concentrate is extracted with dilute aqueous acid (pH 3). The Formula 2 compound may be further purified by chromatography as described herein.

A more preferred technique for isolating the Formula 2 compound from the biomass involves adding an equal volume of acetone to the whole broth, filtering the mixture in a ceramic filter to remove the biomass, and adjusting the pH of the filtrate to about pH 9 to about pH 13. This solution is applied to HP-20SS (Mitsubishi Chemical Industries Co., Ltd., Japan) and the column washed with a mixture of methanol, acetonitrile and water (1:1:2). The Formula 2 compound is eluted with a 95:5 mixture of methanol/ acetonitrile (1:1) and aqueous 0.1% ammonium acetate (pH 8.1). The fractions containing the Formula 2 compounds are combined and lyophilized. The Formula 2 compound may be further purified by chromatography as described herein.

Alternatively, the culture solids, including medium constituents and mycelium, can be used without extraction or separation, but preferably after removal of water, as a source of the Formula 2 compound. For example, after production of the Formula 2 compound, the whole fermentation broth can be dried by lyophilization, by drum-drying, or by azeotropic distillation and drying. The dried broth can then be used directly, for example, by mixing it directly into feed premix or into formulations for sprays and powders.

INSECTICIDE AND MITICIDE ACTIVITY

The Formula 2 compounds are useful for the control of insects and mites. Therefore, a further aspect of the present invention is directed to methods for inhibiting an insect or mite which comprises applying to the locus of the mite or insect an insector mite-inhibiting amount of a Formula 2 compound.

The "locus" of the insect or mite refers to the environment in which the insect or mite lives or where its eggs are present, including the air surrounding it, the food it eats, or objects which it contacts. For example, plant-ingesting insects or mites can be controlled by applying the active compound to plant parts which the insects or mites eat or inhabit, particularly the foliage.

The term "inhibiting an insect or mite" refers to a decrease in the number of living insects or mites or to a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used.

The terms "insect-inactivating amount" and "mite-inactivating amount" are used to describe the amount which is sufficient to cause a measurable reduction in the treated insect or mite population. Generally, an amount in the range from about 1 to about 1,000 ppm (or 0.01 to 1 kg/a) of active compound is used.

The Formula 2 compounds show activity against a number of insects and mites. More specifically, the compounds show activity against beet armyworm and tobacco budworm, which are members of the insect order Lepidoptera. Other typical members of this order are southern armyworm, codling moth, cutworms, clothes moths, indian meal moth, leaf rollers, corn ear worm, cotton bollworm, European corn borer, imported cabbage worm, cabbage looper, pink bollworm, bagworms, eastern tent caterpillar, sod webworm, and fall armyworm.

The Formula 2 compounds also show activity against leaf hoppers, which is a member of the insect order Homoptera. Other members of this order include cotton aphid, plant hoppers, pear psylla, apple sucker, scale insects, whiteflies, and spittle bugs, as well as a number of other host-specific aphid species.

In addition, the Formula 2 compounds show activity against stable flies, blowflies, and mosquitoes, which are members of the insect order Diptera. Another typical member of this order is the common house fly.

The Formula 2 compounds also show activity against two-spotted spider mites, which is a member of the insect order Acarina. Other typical members of this order include mange mite, scab mite, sheep scab mite, chicken mite, scalyleg mite, depluming mite, and dog follicle mite.

The Formula 2 compounds are useful for reducing populations of insects and mites and are used in a method of inhibiting an insect or mite population which comprises applying to a locus of the insect or mite an effective insect- or mite-inactivating amount of a Formula 2 compound. In one preferred embodiment, the present invention is directed to a method for inhibiting a susceptible insect of the order Lepidoptera which comprises applying to a plant an effective insect-inactivating amount of a Formula 2 compound in accordance with the present invention. Another preferred embodiment of the invention is directed to a method of inhibiting biting flies of the order Diptera in animals which comprises administering an effective pest-inhibiting amount of a Formula 2 compound orally, parenterally, or topically to the animal. In another preferred embodiment, the present invention is directed to a method for inhibiting a susceptible insect of the order Homoptera which comprises applying to a plant an effective insect-inactivating amount of a Formula 2 compound. Another preferred embodiment of the invention is directed to a method of inhibiting mites of the order Acarina which comprises applying to the locus of the mite a mite-inactivating amount of a Formula 2 compound.

MITE/INSECT SCREEN

The Formula 2 compounds were tested for miticidal and insecticidal activity in the following mite/insect screen. Each test compound was formulated by dissolving the compound in an acetone-alcohol (1:1) mixture containing 23 g of TOXIMUL R (sulfonate/nonionic emulsifier blend) and 13 g of TOXIMUL S (sulfonate/nonionic emulsifier blend) per liter. These mixtures were then diluted with water to give the indicated concentrations.

Two-spotted spider mites and cotton aphids were introduced on squash cotyledons and allowed to establish on both leaf surfaces. The leaves were then sprayed with 5 ml of test solutions using a DeVilbiss atomizing sprayer at 10 psi. Both surfaces of the leaves were covered until run off and then allowed to dry for one hour. After standard exposure periods percent mortality was evaluated. Additional insects were evaluated using similar formulations and evaluation procedures. The results are reported in Table V. The following abbreviations are used:

| Abbreviation | Pest | Scientific Name |
|---|---|---|
| ALH | Aster Leafhopper | *Macrosteles fascifrons* |
| BAW | Beet Armyworm | *Spodoptera exiqua* |
| CA | Cotton Aphid | *Aphis gossypii* Glover |
| GECR | German Cockroach | *Blattella germanica* |
| NEM | Rootknot Nematode | Meliiodyne spp. |
| SCRW | Southern Corn Rootworm | *Diabrotica undecimpunctata howardi* |
| TBW | Tobacco Budworm | *Heliothis virescens* |
| TSSM | Two-spotted Spider Mite | *Tetranychus urticae* |

TABLE V

Activity of Formula 2 Compounds in Insect/Mite Screen

| Pest | rate[a] | per[c] | % Inhibition[b] A83543Q | A83543R | A83543S | A83543T |
|---|---|---|---|---|---|---|
| ALH | 50 | 24 hr | 100 | 0 | 60 | 20 |
|  | 400 | 24 hr | 100 | 0 | 100 | 100 |
| BAW | 50 | 6 day | 100 | 0 | 100 | 0 |
|  | 400 | 6 day | 100 | 0 | 100 | 0 |
| CA | 50 | 4–5 day | 0 | 0 | 0 | 0 |
|  | 400 | 4–5 day | 0 | 0 | 0 | 0 |
| GECR | 50 | 7 day | 0 | 0 | 0 | 0 |
|  | 400 | 7 day | 0 | 0 | 0 | 0 |

TABLE V-continued

Activity of Formula 2 Compounds in Insect/Mite Screen

| | | | % Inhibition[b] | | | |
|---|---|---|---|---|---|---|
| Pest | rate[a] | per[c] | A83543Q | A83543R | A83543S | A83543T |
| | 50 | 21 day | 0 | 20 | 0 | 0 |
| | 400 | 21 day | 0 | 0 | 20 | 0 |
| NEM | 400 | 11 day | 0 | 0 | 0 | 0 |
| SCRW | 400 | 11 day | 0 | 0 | 0 | 0 |
| TBW | 21 | 6 day | 100 | 63 | 26 | 0 |
| | 64 | 6 day | 100 | 88 | 53 | 0 |
| TSSM | 50 | 4–5 day | 70 | 85 | 0 | 0 |
| | 400 | 4–5 day | 100 | 90 | 0 | 0 |

[a]rate in ppm
[b]% inhibition as a mean of single replicate tests
[c]exposure period.

The Formula 2 compounds were evaluated in the following assay to determine the $LD_{50}$ against neonate tobacco budworm (*Heliothis virescens*). A petri dish (100 mm ×20 mm) is inverted and the lid lined with a #1 qualitative filter paper. Ten neonate larvae are placed in each dish and a 1 ml test solution is pipetted onto the insects. The petri dish bottom is then placed on the lid to contain the larvae. At 1 hr. after treatment, a small piece of Heliothis diet (modified slurry, Southland Products, Lake Village, Ark.) is added to each dish. The mortality is evaluated at 24 and 48 hours. The tests were run in triplicate. The results are shown in Table VI.

TABLE VI

Activity Against Neonate Tobacco Budworm

| Compound | $LD_{50}$ (ppm)[a] |
|---|---|
| A83543Q | 0.39 |
| A83543R | 14.5 |
| A83543S | 53 |
| A83543T | >64 |

[a]mean of two tests

INSECTICIDAL COMPOSITIONS

The Formula 2 compounds are applied in the form of compositions, which are also a part of this invention. These compositions comprise an insect- or mite- inactivating amount of a Formula 2 compound in a phytologically acceptable, inert carrier. The active component, the Formula 2 compound, may be present as a single Formula 2 compound, a mixture of two or more Formula 2 compounds, a mixture of at least one of A83543Q, A83543R, A83543S and A83543T or a mixture of at least one of A83543Q, A83543R, A83543S and A83543T together with the dried portion of the fermentation medium in which it is produced.

Compositions are prepared according to procedures and formula which are conventional in the agricultural chemical art, but which are novel and important because of the presence of one or more of the compounds of this invention. The compositions are either concentrated formulations which are dispersed in water for application or dust or granular formulations which are applied without further treatment.

The dispersions in which the compound or crude dried material are applied are most often aqueous suspensions or emulsions prepared from concentrated formulations of the compounds or crude material. Such water-soluble, water-suspendible, or emulsifiable formulations are either solids (usually known as wettable powders) or liquids (usually known as emulsifiable concentrates or aqueous suspensions).

Wettable powders, which may be compacted to form water dispersible granules, comprise an intimate mixture of the active compound, an inert carrier, and surfactants. The concentration of the active compound is usually from about 1% to about 90% by weight. The inert carrier is usually chosen from among attapulgite clays, the montmorillonite clays, the diatomaceous earths or the purified silicates.

Effective surfactants, comprising from about 0.5% to about 10% of the wettable powder are found among the sulfonated lignins, the condensed naphthalene-sulfonates, the napthalene- sulfonates, the alkylbenzenesulfonates, the alkylsulfates, and nonionic surfactants such as ethylene oxide adducts of alkylphenols.

Emulsifiable concentrates of the compounds comprise a convenient concentration of a compound, such as from about 50 to about 500 grams per liter of liquid, equivalent to about 10% to about 50%, dissolved in an inert carrier which is either a water-miscible solvent or mixture of a water-immiscible organic solvent and emulsifiers. Useful organic solvents include aromatics, especially the xylenes, and petroleum fractions, especially high-boiling naphthlenic and olefinic portions of petroleum such as heavy or aromatic naphtha. Other organic solvents may also be used, such as the terpenic solvents, including rosin derivatives, aliphatic ketones such as cyclohexanone, and complex alcohols such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention dispersed in an aqueous vehicle at a concentration in the range from about 5% to about 50% by weight. The suspensions are prepared by finely grinding the compound, and vigorously mixing it into a vehicle comprised of water and surfactants chosen from the same types discussed above. Inert ingredients, such as inorganic salts and synthetic or natural gums may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The Formula 2 compounds may also be applied as granular compositions, which are particularly useful for applications to the soil. Granular compositions usually contain from about 0.5% to about 10% by weight of the Formula 2 compound, dispersed in an inert carrier which consists entirely or in large part of clay or a similar inexpensive substance. Such compositions are usually prepared by dissolving thee compound in a suitable solvent and applying it to a granular carrier which has been pre-formed to the appropriate particle size in the range of from about 0.5 to 3 mm. Such compositions may also be formulated by making a dough or paste of the carrier, drying the combiined mixture of the active ingredient in the dough Or paste, and crushing the dried composition to obtain the desired granular particle size.

Dusts containing the compound are prepared by intimately mixing the compound in powdered form with a suitable dust agricultural carrier, such as kaolin clay, ground volcanic rock, and the like. Dusts can suitably contain from about 1% to about 10% of the Formula 2 compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are usually applied in the form of a dispersion of the active ingredient in a liquid carrier. It is conventional to refer to application rates in terms of the concentration of active ingredient in the carrier. The most widely used carrier is water.

The Formula 2 compounds can also be applied in the form of an aerosol composition. In such compositions the active compound is dissolved in an inert carrier, which is a pressure-generating propellant mixture. The aerosol composition is packaged in a container from which the mixture is dispersed through an atomizing valve. Propellent mixtures comprise either low-boiling halocarbons, which may be mixed with organic solvents, or aqueous suspensions pressurized with inert gases or gaseous hydrocarbons.

The amount of compound to be applied to the loci of insects and mites is not critical and can readily be determined by those skilled in the art in view of the examples provided. In general, concentrations of from about 10 ppm to about 5,000 ppm of the Formula 2 compound are expected to provide good control. With many of the compounds, concentrations of from about 100 to about 1,000 ppm will suffice. For field crops, such as soybeans and cotton, a suitable application rate for the compounds is about 0.01 to about 1 kg/ha, typically applied in a 5 to 50 gal/A of spray formulation.

The locus to which a Formula 2 compound is applied can be any locus inhabited by an insect or mite, for example vegetable crops, fruit and nut trees, grape vines and ornamental plants. Because of the unique ability of mite eggs to resist toxicant action, repeated applications may be desirable to control newly emerged larvae, as is true of other known acaricides.

ECTOPARASITICIDE ACTIVITY

Tables VII and VIII summarize in vitro studies using compounds of the present invention against members of the insect order Diptera.

TABLE VII

Activity Against Blowfly Larvae

Activity

| Compound | rate (ppm) | % mortality 24 hrs. | 48 hrs. |
|---|---|---|---|
| A83543Q | 10 | 100 | 100 |
|  | 5 | 90 | 90 |
| A83543R | 10 | 100 | 100 |
|  | 5 | 90 | 100 |
| A83543S | 10 | 60 | 60 |
|  | 5 | 0 | 0 |
| A83543T | 100 | 0 | 0 |
|  | 50 | 0 | 0 |

TABLE VIII

Activity Against Adult Stablefly

| Compound | rate (ppm) | % mortality 24 hrs | 48 hrs |
|---|---|---|---|
| A83543Q | 10 | 90 | 100 |
|  | 5 | 50 | 90 |
| A83543R | 10 | 90 | 100 |
|  | 5 | 70 | 100 |
| A83543S | 100 | 90 | 100 |
|  | 50 | 100 | 100 |
| A83543T | 100 | 80 | 90 |
|  | 50 | 60 | 70 |

ECTOPARASITICIDAL METHODS

The ectoparasiticidal method of this invention is carried out by administering a Formula 2 compound to host animals to control insect and Acarina parasites. Administration to the animal may be by the dermal, oral, or parenteral routes.

Parasitic insects and Acarina include species that are bloodsucking as well as flesh eating and are parasitic during all of their life cycle or only part of their life cycle, such as only the larval or only the adult stage. Representative species include the following:

| | |
|---|---|
| horse fly | Tabanus spp. |
| stable fly | Stomoxys calcitrans |
| black fly | Simulium spp. |
| horse sucking louse | Haematopinus asini |
| mange mite | Sarcoptes scabiei |
| scab mite | Psoroptes equi |
| horn fly | Haematobia irritans |
| cattle biting louse | Bovicola bovis |
| shortnosed cattle louse | Haematopinus eurysternus |
| longnosed cattle louse | Linognathus vituli |
| tsetse fly | Glossina spp. |
| cattle follicle mite | Demodex bovis |
| cattle tick | Boophilus microplus and B. decoloratus |
| Gulf Coast tick | Amblyomma maculatum |
| Lone Star tick | Amblyomma americanum |
| ear tick | Otobius megnini |
| Rocky Mountain wood tick | Dermacentor andersoni |
| screw-worm fly | Cochliomyia hominivorax |
| assassin bug | Reduvius spp. |
| mosquito | Culiseta inornata |
| brown ear tick | Rhipicephalus appendiculatus |
| African red tick | Rhipicephalus evertsi |
| bont tick | Amblyomma sp. |
| bont legged tick | Hyalomma sp. |
| hog louse | Haematopinus suis |
| chigoe | Tunga penetrans |
| body louse | Haematopinus ovillus |
| foot louse | Linognathus pedalis |
| sheep ked | Melophagus ovinus |
| sheep scab mite | Psoroptes ovis |
| greenbottle fly | Phaenicia sericata |
| black blow fly | Phormia regina |
| secondary screw-worm | Cochliomyia macellaria |
| sheep blow fly | Phaenicia cuprina |
| bed bug | Cimex lectularius |
| Southern chicken flea | Echidnophaga gallinacea |
| fowl tick | Argas persicus |
| chicken mite | Dermanyssus gallinae |
| scalyleg mite | Knemidokoptes mutans |
| depluming mite | Knemidokoptes gallinae |
| dog follicle mite | Demodex canis |
| dog flea | Ctenocephalis canis |
| American dog tick | Dermacentor variabilis |

| brown dog tick | *Rhipicephalus sanguineus* |

The method of the invention may be used to protect economic and companion animals from ectoparasites. For example, the compound may beneficially be administered to horses, cattle, sheep, pigs, goats, dogs, cats and the like, as well as to exotic animals such as camels, llamas, deer and other species which are commonly referred to as wild animals. The compound may also beneficially be administered to poultry and other birds, such as turkeys, chickens, ducks and the like. Preferably, the method is applied to economic animals, and most preferably to cattle and sheep.

ECTOPARASITICIDAL COMPOSITIONS

This invention also relates to compositions for controlling a population of insect ectoparasites which consume blood of a host animal. These compositions may be used to protect economic, companion, and wild animals from ectoparasites. The compositions may also beneficially be administered to poultry and other birds.

Preferably, the method is applied or the compositions are used to protect economic animals, and most preferably to cattle and sheep. The rate, timing and manner of effective application will vary widely with the identity of the parasite, the degree or parasital attack and other factors. Applications can be made periodically over the entire life span of the host, or for only peak season of parasitic attack. In general ectoparasite control is obtained with topical application of liquid formulations containing from about 0.0005 to about 95% of the Formula 2 compound, preferably up to 5%, and most preferably up to 1% of a Formula 2 compound. Effective parasite control is achieved at an administration rate from about 5 to about 100 mg/kg.

The Formula 2 compounds are applied to host animals by conventional veterinary practices. Usually the compounds are formulated into ectoparasiticidal compositions which comprise a Formula 2 compound and a physiologically-acceptable carrier. For example, liquid compositions may be simply sprayed on the animals for which ectoparasiticidal control is desired. The animals may also treat themselves by such devices as back rubbers which may contain the Formula 2 compound and a cloth, for example, which the animal may walk against in contact. Dip tanks are also employed to administer the active agent to the host animal.

Oral administration may be performed by mixing the compound in the animals' feed or drinking water, or by administering dosage forms such as tablets, capsules, boluses or implants. Percutaneous administration is conveniently accomplished by subcutaneous, intraperitoneal, and intravenous injection of an injectible formulation.

The Formula 2 compounds can be formulated for oral administration in the usual forms, such as drenches, tablets or capsules. Such compositions, of course, require orally-acceptable inert carriers. The compounds can also be formulated as an injectible solution or suspension, for subcutaneous, dermal, intraruminal, intraperitoneal, intramuscular, or intravenous injection. In some applications the compounds are conveniently formulated as one component of a standard animal feed! In this embodiment it is usual to formulate the present compound first as a premix in which the compound is dispersed in a liquid or particulate solid carrier. The premix can contain from about 2 to about 250 g of Formula 2 compound per pound of mix. The premix is in turn formulated into the ultimate feed by conventional mixing.

Because ectoparasitic attack generally takes place during a substantial portion of the host animal's life span, it is preferred to administer Formula 2 compounds in a form to provide sustained release over a period of time. Conventional procedures include the use of a matrix which physically inhibits dissolution, where the matrix is a waxy semi-solid, such as the vegetable waxes, or a high molecular weight polyethylene glycol. A good way to administer the compounds is by means of a sustained-action bolus, such as those of Laby, U.S. Pat. No. 4,251,506 and Simpson, British Patent No. 2,059,767. For such a bolus the compound would be encapsulated in a polymeric matrix such as that of Nevin, U.S. Pat. No. 4,273,920. Sustained release of the compounds of the present invention can also be achieved by the use of an implant such as from a silicone-containing rubber.

In order to illustrate more fully the operation of this invention, the following examples are provided:

EXAMPLE 1

Assay Method for A83543Q, A83543R, A83543S, A83543T

The following analytical high performance liquid chromatography (HPLC) method is useful for monitoring a fermentation for the production of A83543Q, A83543R, A83543S, A83543T and other A83543 components:

A sample of the whole broth is diluted with three volumes of acetonitrile to extract the components from the mycelia. The resulting solution is then filtered through a 0.45 micron polytetrafluoroethylene (PTFE) filter to remove particulate matter prior to injection into the HPLC assay system. A solution of purified A83543A at a concentration of 1 mg/ml in methanol is used as an external standard for the assay and peak areas of all A83543 components are related back to this calibration standard to determine concentrations of individual components.

HPLC System:

Column Support: 4.6×100-mm column, ODS-AQ, 5µ spherical particles, 120Å pore (YMC, Inc., Morris Plains, N.J.)

Mobile Phase: $CH_3CN/MeOH/H_2O$ (37.5/37.5/25) containing 0.05% ammonium acetate

| Flow Rate: | 2 mL/min |
|---|---|
| Detection: | UV at 250 nm |
| Retention Times: | |
| A83543A | 14.97 min |
| A83543Q | 11.82 min |
| A83543R | 4.52 min |
| A83543S | 6.50 min |
| A83543T | 5.97 min |
| A83543H | 8.50 min |

EXAMPLE 2

Preparation of A83543Q, A83543R, A83543S and A83543T with Culture A83543.9

A. Shake-flask Fermentation

The culture *S. spinosa* NRRL 18823, either as a lyophilized pellet or as a suspension maintained in liquid nitrogen, was used to inoculate a vegetative medium having the following composition:

Vegetative Medium 1

| Ingredient | Amount (g) |
| --- | --- |
| Trypticase Broth* | 30 |
| Yeast extract | 3 |
| $MgSO_4.7H_2O$ | 2 |
| Glucose | 5 |
| Deionized water | q.s. 1 L |
| Autoclave 30 min at 120° C. | |

*Baltimore Biological Laboratories, Cockeysville, MD

The first-stage medium may be inoculated from a liquid nitrogen ampoule. Such ampoules are prepared by homogenizing a vegetative culture (48–72 hours incubation, 30° C.) diluting 1:1 (volume:volume) with a sterile suspending agent, and dispensing into sterile tubes (1.5 ml/tube). The suspending agent contains lactose (100 g), glycerol (200) ml, and deionized water (q.s. to 1 L).

A liquid nitrogen ampoule is used to inoculate 50 ml of vegetative medium in 250-ml wide-mouthed Erlenmeyer flasks. The cultures are incubated at 32° C. for 48 hours on a shaker orbiting in a two-inch (5.08 cm) circle at 250 rpm.

The incubated culture (5% v/v inoculum) is used to inoculate 50 ml Erlenmeyer flask, of a production medium having the followimg composition:

Production Medium

| Ingredient | Amount (g) |
| --- | --- |
| Glucose | 80 |
| Peptonized milk* | 20 |
| Cottonseed flour** | 30 |
| Corn steep liquor | 10 |
| $CaCO_3$ (tech. grade) | 5 |
| Methyl oleate | 30*** |
| Tap water | q.s. to 1 L | pH adjusted to pH 7.0 with 1N NaOH, sterilized 40 min. at 120° C.
*Peptonized Milk Nutrient, Sheffield Products, Norwich, NY
**Proflo, Traders Protein, Memphis, TN
***The amount of methyl oleate was 30 ml The inoculated production medium is incubated in 250-ml Erlenmeyer flasks at 30° C. for 7 days on a shaker orbiting in a two-inch circle at 250 rpm.

B. Stirred Reactor Fermentation

In order to provide a larger volume of inoculum, 10 ml of incubated first stage medium, prepared as described in Example 2, Section A, is used to inoculate 400 ml of a second-stage vegetative medium having the same composition as that of the first-stage medium. This second-stage vegetative medium is incubated in a 2 L wide-mouth Erlenmeyer flask for about 48 hours at 32° C. on a shaker orbiting in a two-inch circle at 260 rpm. Incubated second-stage vegetative medium (2 L) thus prepared is used to inoculate 115 liters of sterile production medium, prepared as described in Example 2, Section A.

The inoculated production medium is allowed to ferment in a 165 L stirred bioreactor for 7 days at a temperature of 30° C. The air-flow and agitator speed in the stirred vessel are computer controlled to maintain a dissolved oxygen level at or above 60% to about 80% of air saturation.

EXAMPLE 3

Isolation of A83543Q, A83543R, A83543S and A83543T from A83543.9

Fermentation broth (100 L; harvest titer A83543H, 303 µg/ml, A83543Q, 50 µg/ml), prepared as described in Example 2, was refrigerated two days prior to processing. Acetone (100 L) was added to the whole broth after adjusting the pH to 3.0 with 5N HCl. The resulting mixture was filtered through a ceramic filter to give filtrate (170 L) which was held over the weekend under refrigeration. The broth/acetone filtrate was adjusted to pH 13 and refiltered through the ceramic filter prior to loading onto a steel column (10 L; 10 cm ×122 cm) containing HP-20SS resin (Mitsubishi Chemical Industries, Ltd., Japan) at a flow rate of 1 L/minute. The column was eluted at a flow rate of 1 L/minute with a gradient mixed from solvent "A" (0.1% aq. NH4OAc, adjusted to pH 8.1 with NH4OH) and solvent "B" ($CH_3CN$—$CH_3OH$ 1:1), collecting 4 L fractions. The pumping system was programmed to generate a gradient from 0 to 50% B in one minute, followed by a gradient from 50 to 100% B in 90 minutes, followed by isocratic delivery of 100% B for an additional 15 minutes. HPLC analysis indicated that fraction 17 (4 L), contained predominantly component R with additional more polar materials and a small amount of components T and H; fractions 18–22 contained predominantly component H with lesser amounts of components R and Q and small amounts of components S and more polar materials fractions 23–24 contained components H and Q. HPLC analysis of the pools suggested the following total quantities: component H, 23.0 g; component Q, 3.4 g; component R, 2.0 g; component S, 0.2 g; component T, 0.2 g.

EXAMPLE 4

Recovery of A83543Q, A83543R, AS83543S, and A83543T from a Q-Producing Strain

Fermentation broth (85 L; harvest titer A83543H, 302 µg/ml, A83543Q, 44 µg/ml), prepared as Q-producing strain, was refrigerated overnight prior to processing. Acetone (90 L) was added to the whole broth after adjusting the pH to 3.0 with 5N HCl. The resulting mixture was filtered through a ceramic filter to give filtrate (176 L) which was held over the weekend under refrigeration. The broth/acetone filtrate was adjusted to pH 13 with 50% NaOH and refiltered through the ceramic filter (140 L flitrate) prior to loading onto a steel column (10 L; 10 cm×122 cm) containing HP-20SS resin (Mitsubishi Chemical Industries, Ltd., Japan) at a flow rate of 1 L/minute. The column was eluted at a flow rate of 1 L/minute with a gradient mixed from solvent "A" (0.1% NH4OAc, adjusted to pH 8.1 with $NH_4OH$) and solvent "B" ($CH_3CN$—$CH_3OH$ 1:1), collecting 4 L (approx.) fractions. The pumping system was programmed to generate a gradient from 0 to 50% B in one minute, followed by a gradient from 50 to 100% B in 90 minutes, followed by isocratic delivery of 100% B for an additional 10 minutes. HPLC analysis indicated that pool 1 (fractions 16–21; 24.5 L), contained components H (12.32 g) and Q (0.34 g) pool 2 (fractions 22–25; 16 L) contained components H (4.66 g), Q (2.06 g), R, S and T.

A. Isolation of pure component Q

Pool 2 was concentrated to dryness, redissolved in dichloromethane (50 ml), and applied to a glass column (5.5 cm×30 cm) containing silica gel (EM grade 62, 60–200 mesh) equilibrated in dichloromethane. The column was washed with dichloromethane (3 L), then developed with dichloromethane - methanol (95.5), collecting 250 ml fractions. Fractions 3 through 15 were combined and concentrated to residue, then dissolved in ethanol/water (400 ml) and allowed to stand at room temperature over the weekend. The resulting crystals were washed with cold ethanol/water (1:1) and dried to give 6.1 g of dried crystals containing 68.7% component H and 31.2% component Q, by HPLC analysis.

The dried crystalline material was dissolved in tetrahydrofuran/methanol (1:1) and applied to a preparative reverse phase HPLC column (Rainin Dynamax-60A 8 μm C18, 41.4 mm ID×25 cm with 41.4 mm×5 cm guard module) in 12 runs. The column was eluted at a flow rate of 50 ml/minute with a gradient mixed from solvent "A" ($H_2O$—$CH_3CN$; 30:35:35 containing 0.1% NH4OAC) and solvent "B" ($H_2O$—$CH_3CN$—$CH_3OH$; 10:45:45 containing 0.1% NH4OAC). The pumping system was programmed to generate a gradient from 50 to 100% B in 60 minutes. Progress of the separation was monitored with a variable wavelength UV detector tuned to 250 nm. Peak 1, containing component H (99%; 6 L) eluted first, followed by component Q. Combined peak 2 (containing component H, 20%, component Q, 80%; 8 L) from all (12) runs was concentrated to 500 ml, reapplied to the same column, and eluted under the same mobile phase conditions in 5 runs. Pool 2 (2 L), containing 99% pure component Q was desalted by applying it to the same, column equilibrated in $H_2O$—$CH_3OH$—$CH_3CN$ (20:40:40). The column was eluted with $H_2O$—$CH_3OH$—$CH_3CN$ (10:45:45), collecting 10 three-minute fractions. Fractions 2 through 7 were combined, concentrated to residue, and dissolved in hot EtOH (80 ml). An equal volume of $H_2O$ was added and the solution was allowed to cool overnight. The resulting crystals were collected on a filter, washed with cold EtOH—$H_2O$ (1:1), and dried to give 1.5 g pure A83543Q.

B. Isolation of pure component R

Pool 1 from the HP-20SS chromatography was concentrated to residue and dissolved in methanol (200 ml). The component H- and Q-containing solution was precipitated into acetonitrile (3 L) and then filtered. The filtrate was concentrated to dryness, then dissolved in dichloromethane (100 ml) and applied to a glass column (5.5 cm×30 cm) Containing silica gel (EM grade 62, 60–200 mesh) equilibrated in dichloromethane. The column was washed with dichloromethane (2 L), then developed with dichloromethane - methanol (95:5), collecting 250 ml fractions. (Fractions 3 through 7, containing components S and T are discussed below, under isolation of pure components S and T.) Fractions 9 through 14 were combined and concentrated to residue, then dissolved in $CH_3OH$ (10 ml) and applied to a preparative reverse phase HPLC column (Rainin Dynamax-60A 8 μm C18, 41.4 mm ID×25 cm with 41.4 mm×5 cm guard module) equilibrated in ($H_2O$—$CH_3OH$—$CH_3CN$; 30:35:35 containing 0.1% NH4OAC) and solvent "B" ($H_2O$—$CH_3CN$—$CH_3OH$; 25:87.5:87.5 containing 0.1% NH4OAC). The pumping system was programmed to generate a gradient from 0 to 100% B in 60 minutes. Progress of the separation was monitored with a variable wavelength UV detector tuned to 25 nm. The fraction containing the major peak was desalted by applying it to the same column and eluting with a 60 minute gradient from $H_2O$—$CH_3OH$—$CH_3CN$ (30:35:35) to $H_2O$—$CH_3OH$—$CH_3CN$ (10:45:45), collecting 12 five-minute fractions. Fractions 2 through 12 were concentrated to residue, dissolved in t-BuOH, and lyophilized to give 1.77 g pure A83543R.

C. Isolation of pure components S and T

Fractions 3 through 7 from the dichloromethanemethanol (95:5) elution of the silica gel column (see Example 4, Section B) were combined, concentrate to residue, and dissolved in EtOH—$H_2O$ (1:1 and allowed to stand at room temperature over the weekend. The resulting crystals were harvested by filtration and, washed with cold EtOH—$H_2O$ (1:1), and dried to give 5.4 g of crystalline materials. The combined filtrate and wash were applied (in 10 runs) to a preparative reverse phase HPLC column (Rainin Dynamax-60A 8 μm C18, 41.4 mm ID×25 cm with 41.4 mm×5 cm guard module) equilibrated in (0.5% aq. NH4OAc $CH_3OH$—$CH_3CN$; 20:40:40). The column was eluted at a flow rate of 40 ml/minute with a gradient mixed from solvent "A" ($H_2O$—$CH_3OH$—$CH_3CN$; 30:35:35 containing 0.1% NH4OAC) and solvent "B" ($H_2O$—$CH_3CN$—$CH_3OH$; 10:45:45 containing 0.1% NH4OAC). The pumping system was programmed to generate a gradient from 50 to 100% B in 60 minutes. Progress of the separation was monitored with a variable wavelength UV detector tuned to 250 nm; the major UV peak was collected in 4 pools. Pool 1 (5 L) contained component S; pool 5 (5 L), eluting ahead of the major UV peak, contained component T. The 5.4 g crystalline materials (see above) were dissolved, applied to the same column, and eluted under the same protocol to give pool 1 (5 L) containing component T and pool 2 (2 L) containing component S, followed by components H and Q.

The component S containing pools from the two RP-HPLC prep runs were combined, concentrated to residue, redissolved in 5 ml $CH_3OH$, and chromatographed on the same column with the same mobile phase gradient. Two UV absorbing (250 nm) peaks were collected. Peak 2 contained component H. Peak 1, containing component S was concentrated to 50 ml and applied to a Rainin Dynamax-60A 8 μm C18, 21.4 mm D×25 cm column with 21.4 mm×5 cm guard module) equilibrated in $H_2O$—$CH_3OH$—$CH_3CN$ (40:30:30). The column was eluted at a flow rate of 10 ml/minute with a gradient mixed from solvent "A" ($H_2O$—$CH_3OH$—$CH_3CN$; 40:30:30) and solvent "B" ($H_2O$—$CH_3OH$—$CH_3CN$; 10:45:45 with 0.1% NH4OAc and 1% HOAc added). The pumping system was programmed to generate a gradient from 10 to 30% B in 60 minutes. The major UV absorbing peak was collected, concentrated to ½ volume, and desalted on the same HPLC column equilibrated in $H_2O$—$CH_3OH$—$CH_3CN$; 40:30:30, eluting with a 60 minute gradient from $H_2O$—$CH_3OH$—$CH_3CN$; (40:30:30) to $H_2O$—$CH_3OH$—$CH_3CN$ (10:45:45), collecting 2 minute fractions. Fractions 2 through 8 were pooled and concentrated to dryness. The residue was dissolved in t-BuOH (5 ml) and lyophilized to give pure component S (182 mg).

The component T-containing pools from the two reverse phase HPLC (RP-HPLC) prep runs were combined, concentrated to 100 ml, and applied (in 4 runs) to a preparative RP-HPLC column (Rainin Dynamax-60A 8 μm C18, 21.4 mm ID×25 cm with 21.4 m×5 cm guard module) equilibrated in $H_2O$—$CH_3OH$—$CH_3CN$ (30:35:35 containing 0.1% NH4OAC). The column was eluted at a flow rate of 10 ml/minute with a gradient mixed from solvent "A" ($H_2O$—$CH_3OH$—$CH_3CN$; 30:35:35 containing 0.1% NH4OAC) and solvent "B" ($H_2O$—$CH_3OH$ $CH_3CN$; 10:45:45 containing 0.1% NH4OAC). The pumping system was programmed to generate a gradient from 25 to 75% B in 60 minutes. One peak contained pure component R. The other peak, containing a mixture of components R and T, was rechromatographed under the same conditions. The pure component T containing peak from the latter HPLC preparative run was desalted on the same column equilibrated in $H_2O$—$CH_3OH$—$CH_3CN$ (30:35:35) and eluted with $H_2O$—$CH_3OH$—$CH_3CN$ (10:45:45). The UV absorbing peak was concentrated to dryness. The residue was dissolved in t-BuOH and lyophilized to give pure component T (166 mg).

We claim:

1. A process for preparing a compound of Formula 2:

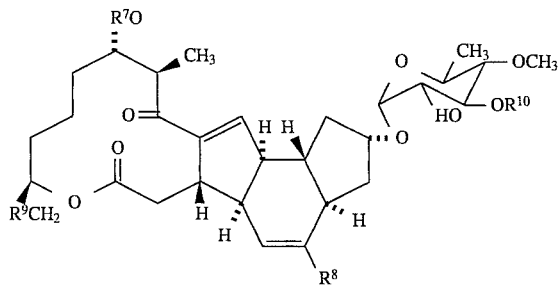

where $R^7$ is a group of formula

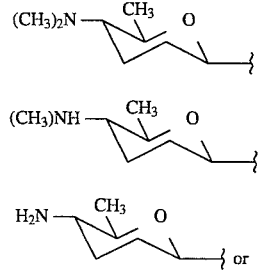

and $R^8$, $R^9$ and $R^{10}$ are independently hydrogen or methyl; provided that when both $R^7$ is

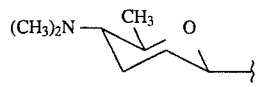

and $R^8$ is hydrogen then $R^9$ and $R^{10}$ are not both methyl, which comprises cultivating *S. spinosa* strain NRRL 18823 or a mutant thereof, in a suitable culture medium, under submerged aerobic fermentation conditions until a recoverable amount of a compound of Formula 2 is produced and then recovering said compound of Formula 2.

2. The process of claim 1 further comprising the step of separating the compound of Formula 2, wherein $R^7$ is (a), $R^8$ is Me, $R^9$ is Me and $R^{10}$ is Me.

3. The process of claim 1 further comprising the step of separating the compound of Formula 2, wherein $R^7$ is (b), $R^8$ is H, $R^9$ is Me, $R^{10}$ is Me.

4. The process of claim 1 further comprising the step of separating the compound of Formula 2, wherein $R^7$ is (a), $R^8$ is H, $R^9$ is H and $R^{10}$ is Me.

5. The process of claim 1 further comprising the step of separating the compound of Formula 2, wherein $R^7$ is (a), $R^8$ is H, $R^9$ is Me and $R^{10}$ is H.

* * * * *